US00RE38009E

(19) United States
(12) Reissued Patent
Garnett et al.

(10) Patent Number: US RE38,009 E
(45) Date of Reissued Patent: Feb. 25, 2003 u

(54) ZEAXANTHIN FORMULATIONS FOR HUMAN INGESTION

(75) Inventors: Kevin M. Garnett, Morristown, NJ (US); Luis H. Guerra-Santos, Ballwin, MO (US); Dennis L. Gierhart, Chesterfield, MO (US)

(73) Assignee: Zeavision LLC, St. Louis, MO (US)

(21) Appl. No.: 09/699,985

(22) Filed: Oct. 27, 2000

Related U.S. Patent Documents

Reissue of:

(64) Patent No.: 5,827,652
Issued: Oct. 27, 1998
Appl. No.: 08/551,153
Filed: Oct. 31, 1995

(51) Int. Cl.[7] ..... C12P 23/00; C12N 1/20; A61K 9/48

(52) U.S. Cl. ..... 424/451; 424/455; 424/463; 424/464; 424/474; 424/489; 424/93 R; 424/93 A; 424/93 D; 426/61; 426/89; 426/103; 426/549; 426/550; 426/556; 426/574; 426/581; 426/582; 426/583; 426/586; 426/587; 426/590; 426/599; 426/603; 426/648; 426/652; 426/653; 426/655; 426/807

(58) Field of Search ..... 424/451, 455, 424/463, 464, 474, 489, 93 R, 93 A, 93 D; 426/61, 89, 103, 807, 549, 550, 556, 574, 581, 582, 583, 586, 587, 590, 599, 603, 648, 652, 653, 655

(56) References Cited

U.S. PATENT DOCUMENTS

| | | | | |
|---|---|---|---|---|
| 3,841,967 | A | 10/1974 | Dasek et al. | 195/29 |
| 3,879,424 | A | 4/1975 | Surmatis et al. | |
| 3,891,504 | A | 6/1975 | Schocher et al. | 195/28 R |
| 3,932,462 | A | 1/1976 | Goetz et al. | |
| 3,951,743 | A | 4/1976 | Shepherd et al. | 195/28 R |
| 3,954,804 | A | 5/1976 | Fischer et al. | |
| 3,974,181 | A | 8/1976 | Surmatis et al. | |
| 4,078,094 | A | 3/1978 | Katzen | 426/641 |
| 4,153,615 | A | 5/1979 | Saucy | 260/340.9 R |
| 4,298,621 | A | 11/1981 | Samis et al. | 426/55 |
| 4,405,417 | A | 9/1983 | Grass et al. | |
| 4,522,743 | A | 6/1985 | Horn et al. | 252/311 |
| 4,579,973 | A | 4/1986 | Widmer et al. | |
| 4,726,955 | A | 2/1988 | Horn et al. | 426/73 |
| 4,851,339 | A | 7/1989 | Hills | 435/67 |
| 4,935,409 | A | 6/1990 | Wollweber et al. | 514/63 |
| 4,952,716 | A | 8/1990 | Lukac et al. | 556/482 |
| 5,180,747 | A | 1/1993 | Matsuda | 514/681 |
| 5,227,507 | A | 7/1993 | Lukac et al. | 556/449 |
| 5,242,950 | A | 9/1993 | Fries Hastings | |
| 5,308,759 | A | 5/1994 | Gierhart | 435/67 |
| 5,310,764 | A | 5/1994 | Baranowitz et al. | 514/725 |
| 5,350,773 | A | 9/1994 | Schweikert et al. | 514/763 |
| 5,356,636 | A | 10/1994 | Schneider et al. | 424/489 |
| 5,360,730 | A | 11/1994 | Orndorff et al. | |
| 5,382,714 | A | 1/1995 | Khachik | 568/834 |
| 5,427,783 | A | 6/1995 | Gierhart | 424/93.4 |
| 5,429,939 | A | 7/1995 | Misawa et al. | 435/67 |
| 5,437,997 | A | 8/1995 | Liao et al. | |
| 5,523,494 | A | 6/1996 | Torres-Cardona et al. | 568/834 |
| 5,527,533 | A | 6/1996 | Tso et al. | 424/422 |
| 5,607,839 | A | 3/1997 | Tsubokura et al. | |
| 5,684,238 | A | 11/1997 | Ausich et al. | |
| 5,777,173 | A | 7/1998 | Paust et al. | |
| 5,780,693 | A | 7/1998 | Bernhard et al. | |
| 6,218,436 | B1 | 4/2001 | Howard et al. | |

FOREIGN PATENT DOCUMENTS

| | | |
|---|---|---|
| EP | 0 747 483 A2 | 12/1996 |
| WO | WO96/40092 A1 | 12/1996 |

OTHER PUBLICATIONS

Bendich, A., et al, "Biological actions of carotenoids," *FASEB Journal* 3: 1927–1932 (1989).

Bone, R.A., et al, "Preliminary identification of the human macular pigment," *Vision Res.* 25: 1531–1535 (1985).

Bone R.A., et al, "Stereochemistry of the macular carotenoids," *Invest. Ophthalmol. Vis. Sci.* 34: 2033–2040 (1993).

Columbo, V.E., et al, "Structures and properties of stabilized vitamin and carotenoid dry powders," *Food Structure* 10: 161–170 (1991).

(List continued on next page.)

*Primary Examiner*—Frederick Krass
(74) *Attorney, Agent, or Firm*—Patrick Kelly; Daniel Burnham; Ronald Compton

(57) ABSTRACT

Preparations are disclosed containing the 3R-3'R stereoisomer of zeaxanthin as a sole detectable isomer, packaged for oral ingestion by humans as a therapeutic drug or nutritional supplement. Zeaxanthin is a yellow carotenoid pigment found in the macula (in the center of the human retina), which helps protect retinal cells against phototoxic damage. The pure R-R stereoisomer can be prepared by fermenting cells, such as Flavobacterium multivorum (ATCC 55238), which do not create any detectable quantity of the undesired and potentially toxic S-S or S-R isomers, and which do not synthesize any other carotenoids. The R-R isomer can be concentrated, in large quantities and at low cost, into a viscous oily fluid containing about 5 to 20% zeaxanthin, by means of a simple solvent extraction process. This oily fluid can be mixed with a carrier such as vegetable oil and enclosed within a digestible capsule, comparable to a conventional capsule containing Vitamin E. Alternately, a zeaxanthin fluid can be added to various types of foods, such as margarine, dairy products, syrup, cookie dough, and certain types of meat preparations which are not subjected to harsh cooking. Additional purification steps can also be used to purify zeaxanthin to a granular or powdered state which contains nearly pure zeaxanthin. Such processing can be used to create formulations such as ingestible tablets, and particulate formulations that can be added to soups, salads, drinks, or other foods. Preferred stabilizers and anti-oxidants are also disclosed herein. When consumed by humans in any of these modes, the purified R-R stereoisomer of zeaxanthin can help treat and prevent macular degeneration, one of the leading causes of blindness and vision loss, especially among the elderly.

33 Claims, 2 Drawing Sheets

OTHER PUBLICATIONS di Mascio, P., et al, "Lycopene as the most efficient biological carotenoid singlet oxygen quencher," *Archives of Biochemistry and Biophysics* 274: 532–538 (1989).

di Mascio, P., et al, "Antioxidant defense systems: the role of carotenoids, tocopherols, and thiols," *Am. J. Clin. Nutr.* 53: 194S–200S (1991).

Dorey, C.K., et al, "Lipofuscin in aged and AMD eyes," in *Retinal Degeneration* (Hollyfield et al., editors, Plenum Press, New York, 1993).

Eye Disease Case Control Study Group, "Antioxidant status and neovascular age–related macular degeneration," *Arch. Ophthalmol.* 11: 104–109 (1993).

Eye Disease Case Control Study Group, "Risk factors for neovascular age–related macular degeneration," *Arch. Ophthalmol.* 10: 1701–1708 (1992).

Gerster, H., "Review: antioxidant protection of the ageing macula," *Age and Aging* 20: 60–69 (1991).

Haegerstrom–Portnoy, G., "Short–wavelength–sensitive––cone sensitivity loss with aging: a protective role for macular pigment?," *J. Opt. Soc. Am.* A5: 2140–2144 (1988).

Handelman, G.J. and Dratz, E.A., "The role of antioxidants in the retina and retinal pigment epithelium and the nature of prooxidant–induced damage," *Adv. in Free Radical Biology & Medicine* 2: 1–23 and 55–57 (1986).

Handelman, G.J., et al, "Carotenoids in the human macula and whole retina," *Invest. Ophthalmol. Vis. Sci.* 29: 850–855 (1988).

Malinow, M.R., et al, "Diet–related macular anomalies in monkeys," *Invest. Ophthalmol. Vis. Sci.* 19: 857–863 (1980).

National Advisory Eye Council, *Vision Research Research: A National Plan*, 1994–1998 (NIH Publication 93–3186), pp. 55–64, 336, and 356(1998).

*Requirements of Laws and Regulations Enforced by the U.S. Food and Drug Administration* (excerpt, pp. 9–11), DHHS Publications No. (FDA) 89–1115(1995).

Seddon, J.M., et al, "Dietary carotenoids, vitamins A, C, and E, and advanced age–related macular degeneration," *JAMA* 272: 1413–1420 (1994).

Sperduto, R.D., et al, "Do we have a nutritional treatment for age–related cataract or macular degeneration?," *Arch. Ophthalmol.* 108: 1403–1405 (1990).

Taylor, A., et al, "Oxidation and aging: impact on vision," *Journal of Toxicology and Industrial Health* 9:349–371 (1993).

Waldroup, P.W., "Dietary nutrient allowances for poultry," *Feedstuffs*, pp. 66–74 (Jul. 17, 1996).

DHHS Publication No. (FDA) 89–1115, Requirements of . . . U.S. Food & Drug Admin., pp. 9–11 (1995).

"Flora–Glo Lutein" product specification sheets (Kemin Industries Inc., Des Moines, Iowa, 1997).

Alpers, J.R., et al, "Serum Carotenoids and Age–Related Macular Degeneration," *Invest Ophthalmol Vis Sci* 36: S9 (1995).

Ascherio, A., et al, "Correlations of Vitamin A and E Intakes with the Plasma Concentrations of Carotenoids and Tocopherols among American Men and Women," *J of Nutrition* 122 (9): 1792–1801 (1992).

Bernstein, H.N., et al, "The Pathology of Chloroquine Retinopathy," *Arch Ophthalmol* 71: 238–245 (1964).

Bertram, J.S., et al, "Diverse carotenoids protect against chemically induced neoplastic transformation," *Carcinogenesis* 12 (4): 671–678 (1991).

Blumenkranz, M.S., et al, "Risk factors in age–related maculopathy complicated by choroidal neovascularization," *Ophthalmology* 93: 552–558 (1986).

Bone, R.A., et al, "Distribution of macular pigment stereomers in individual eyes, including those with age–related macular degeneration (AMD)," *Arvo Abstracts Invest Ophthalmol Vis Sci* V.35: 4 pp1502 (1994).

Bone, R.A., et al, "Analysis of the macular pigment by HPLC: retinal distribution and age study," *Invest Ophthalmol Vis Sci* 29: 843–9 (1988).

Bone, R.A., "The role of the macular pigment in the detection of polarized light," *Vision Research* 30: 213–220 (1979).

Bowmaker, J.D., et al, "Visual pigments and oil droplets in genetically manipulated and carotenoid deprived quail: a microspectrophotometric study," *Vision Res* 33: 571–578 (1993).

Burton, G.W., "Antioxidant action of carotenoids," *American Institute of Nutrition,* 109–111 (1988).

Castorina, C., et al, "Lipid peroxidation and antioxidant enzymatic systems in rat retina as a function of age," *Neurochem Res* 17(6): 599–604 (1992).

Christen, W.G., "Antioxidants and eye disease," *The Amer J of Medicine* 97 (suppl 3A): 3A–142–3A–162 (1994).

Conn, P.F., et al, "The singlet oxygen and carotenoid interaction," *J Photochem Photobiol B Biol* 11: 41–47 (1991).

Crary, E.J., "Antioxidant treatment of macular degeneration of the aging and macular edema in diabetic retinopathy," *Southern Med J* 80: 38 (1997).

Fite, K.V., "Drusen–like deposits in the outer retina of Japanese quail," *Exp Eye Res* 59: 417–424 (1994).

Fite, K.V., et al, "Experimental light damage increases lipofuscin in the retinal pigment epithelium of Japanese quail," *Exp Eye Res* 57: 449–460 (1993).

Fite, K.V., et al, "Age, sex and light damage in the avian retina: a model system," P. Bagnoli et al, Ed, *The Changing Visual System*: 283–294 (1991).

Foote, C.S., et al, "Chemistry of singlet oxygen. X. Carotenoid quenching parallels biological protection," *J Amer Chem Soc* 92: 17 (1970).

Goldberg, J., et al, "Factors Associated with Age–Related Macular Degeneration: An analysis of Data from the First National Health and Nutrition Examination Survey," *Am J Epidemiol* 128(4): 700–10 (1988).

Gottsch, J.D., et al, "Hematogenous photosensitization," *Inves Opthamol & Vis Sci* 31(9): 1674–1682 (1990).

Gruszecki, W.I., et al, "Orientation of xanthophylls in phosphatidylcholine multibilayers," *Biochim Biophys Acta* 1023(3): 405–412 (1990).

Ham, W.T., et al, "Basic mechanisms underlying the production of photochemical lesions in the mammalian retina," *Curr Eye Res* 3(1): 165–174 (1984).

Ham, W.T., et al, "The photopathology and nature of the blue–light and near–UV retinal lesions produced by lasers and other optical sources," ed. Plenum Press; New York, *Laser Application in Medicine and Biology*: 191–246 (1989).

Hart, D.J., et al, "Development and evaluation of an HPLC method for the anlaysis of carotenoids in foods, and the measurement of the carotenoid content of vegetables and fruits commonly consumed in the UK," *Food Chem* 54: 101–11 (1995).

Hockwin, O., et al, "Investigations on lens transparency and its disturbances by microdensitometric analyses of Scheimpflug photographs," *Curr Eye Res* 3(1): 15–22 (1984).
Hope, G.M., et al, "A primate model for age related macular drusen," *British J of Ophthalmol* 76: 11–16 (1992).
Kahn, H.A., et al, "Framingham Eye Study 1. Outline and major prevalence finding," *Am J Epidemiol* 106(1): 17–32 (1977).
Khachik, F., et al, "Lutein, lycopene, and their oxidative metabolites in chemoprevention of cancer," *J of Cell Biochem* S22: 236–246 (1995).
Khachik F., et al, "Separation and identification of carotenoids and their oxidation products in the extracts of human plasma," *Anal Chem* 64: 2111–22 (1992).
Kirschfeld, K., "Carotenoid pigments: their possible role in protecting against photooxidation in eyes and photoreceptor sells," *Proc R Soc London* B 216: 71–85 (1982).
Klaui, H. and Bauerenfeind, C.J., pp 86–102 in *Carotenoids as colorants and vitamin A precursors*, Baurenfeind, C.J., Ed, Academic Press (1981).
Klein, R., et al, "Racial/ethnic differences in age–related maculopathy. Third National Health and Nutrition Examination Survey," *Opthamology* 102(3): 371–81 (1995).
Klein, B., et al, "Prevalence of Age–related Lens Opacities in a Population: The Beaver Dam Eye Study," *Ophthalmol* 99(4): 546–52 (1992).
Mangels, A.R., et al, "Carotenoid content of fruits and vegetables: an evaluation of analytical data," *J Amer Diet Assn* 93(3): 284–96 (1993).
Mares–Perlman, J.A., et al, "Serum antioxidants and age–related macular degeneration in a population–based case–control study," *Arch Ophthalmol* 113: 1518–1523 (1995).
Monaco, W.A., et al, "The rhesus monkey as an animal model for age–related maculopathy," *Optometry Vis Sci* 67(7): 532–537 (1990).
Nussbaum, J.J., et al, "Historic perspectivesL Macular yellow pigment. The first 200 years," *Ophthal Comm Soc* 1(4): 296–310 (1981).
Parker, R.S., "Carotenoids in human blood and tissues," *Amer Inst Nutr*: 101–104 (1988).
Pease, P.L., et al, "Optical density of human macular pigment," *Vis Res* 27(5): 705–710.
Sanders, T.A.B., et al, "Essential fatty acids, plasma cholesterol, and fat–soluble vitamins in subjects with age–related maculopathy and matched control subjects," *Am J Clin Nutr* 57: 428–433 (1993).
Schalch, W., "Carotenoids in the retina—a review of their possible role in preventing or limiting damage caused by light and oxygen," Emerit I., et al, Ed, *Free Radicals and Aging*: 280–298 (1992).
Seddon, J.M., et al, "Vitamins, minerals, and macular degeneration: Promising but unproven hypotheses," *Arch Ophthalmol* 112: 176–179 (1994).
Snodderly, D.M., "Evidence for protection against age–related macular degeneration by carotenoids and antioxidant vitamins," *Am J Clin Nutr* 62(Suppl): 1448S–61S (1995).
Snodderly, D.M., et al, "The macular pigment. I. Absorbance spectra, localization, and discrimination from other yellow pigments in primate retinas," *Invest Ophthalmol Vis Sci* 25: 660–673 (1984a).
Snodderly, D.M., et al, "The macular pigment. II. Spatial distribution in primate retinas," *Invest Ophthalmol Vis Sci* 25: 674–85 (1984b).
Snodderly, D.M., et al, "Distribution of individual macular pigment carotenoids in central retina of macaque and squirrel monkeys," *Invest Ophthalmol Vis Sci* 32(2): 268–279 (1991).
Sowell, A.L., et al, "Identification of cis–carotenoids in human sera analyzed by reversed–phase high performance liquid chromatography with diode array detection," *J Chromatog* 431: 424–30 (1988).
Stone, W.L., et al, "A reinvestigation of the fatty acid content of bovine, rat and frog retinal rod outer segments," *Exp Eye Res* 28: 387–397 (1979).
Sunness, J.S., et al, "Diminished foveal sensitivity may predict the development of advanced age–related macular degeneration," *Ophthalmol* 96(3): 375–381 (1989).
Taylor, H.R., et al, "The long–term effects of visible light on the eye," *Arch Ophthalmol* 110: 99–104 (1992).
Thylefors, B., et al, "Global Data on Blindness," *Bulletin of the World Health Organization* 73(1): 115–121 (1995).
Vingerling, J.R., "Epidemiology of age–related maculopathy," *Epidemiol Rev* 17(2): 347–360 (1995).
Weiser, J., et al, "Provitamin A activities and physiological functions of carotenoids in animals: relevance to human health," *Ann NY Acad Sci* 691: 213–215 (1993).
Weiter, J.J., et al, "Central sparing in annular macular degeneration," *Am J Ophthalmol* 106: 286–292 (1988).
Werner, J.S., "Aging and human macular pigment density," *Vis Res* 27(2): 257–268 (1987).
West, S., et al, "Epidemiology of risk factors for age–related cataracts," *Survey Ophthalmol* 39(4): 323–34 (1995).
West, S., et al, "Are antioxidants or supplements protective for age–related macular degeneration?," *Arch Ophthalmol* 112: 222–227 (1994).
National Eye Advisory Council, pp. 13–38 in *Vision Research—A National Plan*: 1999–2003 (NIH Publ. 99–4120, 1999).
Fine, S.L., et al, "Age–related macular degeneration," *New Engl J Med* 342: 483–492 (2000).
Jampol, L.M., "Antioxidants, zinc, and age–related macular degeneration," *Arch Ophthalmol* 119: 1533–1534 (2001).
AREDS Research Group, Report No. 8, "A randomized, placebo–controlled, clinical trial of high–dose supplementation with vitamins C and E, beta carotene, and zinc for age–related macular degeneration and vision loss," *Arch Ophthalmol* 119: 1417–1436 (2001).

ZEAXANTHIN FORMULATIONS FOR HUMAN INGESTION

Matter enclosed in heavy brackets [ ] appears in the original patent but forms no part of this reissue specification; matter printed in italics indicates the additions made by reissue.

BACKGROUND OF THE INVENTION

This invention is in the field of pharmacology, and relates to human use of a yellow pigment called zeaxanthin (ZX) in preventing or treating macular degeneration, a disease which damages retinal tissue and causes blindness.

This application is being simultaneously filed with a related patent application entitled, "Method of Making Pure 3R-3'R Stereoisomer of Zeaxanthin for Human Ingestion," Ser. No. 08/551,166. Both of these two patent applications are assigned to the same assignee (Applied Food Biotechnology, Inc. of O'Fallon, Mo.). The contents of that related application are incorporated herein by reference; upon issuance of a US patent based upon this current application, that related application will be opened for public inspection, if it has not already issued as a US patent.

In addition to describing methods of manufacturing and purifying commercially useful quantities of isomerically pure R-R zeaxanthin, that related patent application contains a fairly extensive discussion of retinal physiology and carotenoid chemistry. Although that Background information will not be repeated herein it its entirety, an overview is provided in the next four paragraphs, to help introduce and explain this invention to those who have not read the other related patent application.

Briefly, there is a yellow region called the macula in the central area of the retina, inside the eyeball. The yellow color is caused by two carotenoid pigments, lutein and zeaxanthin. These carotenoids have a yellow color because they absorb the high-energy radiation of the near-ultraviolet and blue light spectrum and reflect the yellow/yellow-orange wavelengths. It is theorized that since these two pigments absorb wavelengths in the high-energy spectrum, they may help protect retinal cells in the macula against "phototoxic" damage caused by short-wavelength high-energy light radiation.

Lutein and zeaxanthin are chemically very closely related to each other; both have the exact same chemical formulae, differing only in their ring stereochemistry and the spatial placement of one end ring and the placement of a double bond in that end ring, as shown in FIG. 1.

"Macular degeneration" is a medical term that applies to any of several disease syndromes which involve a gradual loss or impairment of eyesight due to cell and tissue degeneration of the yellow macular region in the center of the retina. Age-related macular degeneration (AMD) is the most common form of this type of disease. AMD affects millions of Americans over the age of 60, and is the leading cause of new blindness among the elderly. It is characterized and usually diagnosed by the presence of elevated levels of two types of cellular debris within the retina, called drusen and lipofuscin. These types of cellular debris may accumulate to abnormal levels for a number of reasons, including: (1) retinal cell damage caused by repeated exposure to too much light; (2) inherited genetic factors; (3) poor overall health of an individual; and (4) insufficient quantities of anti-oxidant compounds such as vitamins A, C, and E and selenium in a person's diet. Accumulation of drusen occurs within the capillaries and in the Bruck's membrane, and can impede the transport of oxygen and nutrients to the retinal tissues, and the removal of metabolic wastes from the tissues. Accumulations of lipofuscin occurs within a cellular layer which underlies the photoreceptors and which is responsible for nourishing, replenishing and removing wastes from these highly active visual cells. Accumulation of one or both of these types of debris can disrupt the normal metabolic and cellular processes which must occur in order to maintain retinal and visual health.

Although the presence and the apparent or likely protective role of zeaxanthin in the retina have been recognized for more than a decade, no one has previously been able to create purified zeaxanthin preparations suitable for human consumption, either as drugs for treating macular degeneration, or as vitamin/nutritional supplements for reducing the risk of macular degeneration later in life. This has been a major shortcoming, since there are no other effective means for treating or preventing macular degeneration; although β-carotene, vitamin A, and vitamin E have generally beneficial anti-oxidant effects and may slightly retard the rate of macular degeneration, they do not rise to the level of truly effective treatments. For practical purposes, macular degeneration must be regarded as unpreventable, unstoppable, and irreversible, and anti-oxidants such as β-carotene, vitamin A, and vitamin E are merely palliative measures that can be used to try to slow down the encroaching damage somewhat, since nothing better is available to the public.

The primary (and previously insurmountable) problems that have been encountered in prior efforts to create purified forms of zeaxanthin for human ingestion include: (1) the extremely high level of chemical similarity between zeaxanthin and other less desirable carotenoids, including lutein and β-carotene, make it extremely difficult to separate zeaxanthin from lutein and β-carotene on any commercial scale; and, (2)zeaxanthin itself has three different stereoisomers, called the 3R-3'R isomer (which is desirable, and which is present in retinal cells), the 3S-3'S isomer (which is undesirable and which is not believed to exist naturally in retinal cells) and the S-R meso isomer. The S-R meso isomer is not normally ingested in the human diet, and is not present in human blood, but it is sometimes found in the retina, apparently as a conversion product that is sometimes created when lutein is chemically altered by high-energy light waves. Although hard scientific evidence of its roles and effects in the retina is not yet available, the S-R meso isomer of zeaxanthin is presumably less desirable than the naturally occurring R-R isomer.

It is effectively impossible to separate these three isomers of zeaxanthin from each other in commercial quantities; therefore, synthetic methods of creating racemic (mixed-isomer) mixtures of zeaxanthin are effectively useless in efforts to create zeaxanthin for human ingestion. In addition, although it is theoretically possible to chemically synthesize enriched formulations having reduced quantities of the undesired S-S and S-R isomers, the necessary chemical techniques are extremely difficult and expensive, and have never been commercialized.

That completes an overview of the scientific and medical background of this invention: as mentioned above, these topics are discussed in more detail in the related patent application cited above.

Prior Art Involving Zeaxanthin Synthesis

In analyzing the prior art, it must be recognized that zeaxanthin has been known for more than a decade to be present in the retina, and scientists have hypothesized for at least that long that zeaxanthin appears to play a beneficial protective role in helping prevent phototoxic damage in the retina. However, no one prior to this invention has ever been able to synthesize the purified R-R stereoisomer of zeaxanthin in any quantities sufficient for human consumption. This failure can be attributed to the extraordinary difficulties of (1) separating zeaxanthin from other carotenoids, and (2) isolating the desired R-R isomer of zeaxanthin and removing the undesirable S-S and S-R isomers.

Accordingly, As of October 1995, the only way to purchase zeaxanthin, either in purified form or in a semi-concentrated form in which zeaxanthin comprises more than about 5% of the weight of the preparation, requires the purchase of very small quantities of zeaxanthin (measured in milligrams) from specialty chemical manufacturers such as Atomergic Chemicals Corporation (Farmingdale, N.Y.) or Spectrum Chemical Manufacturing Company (Gardena, Calif.). The 1995 prices of purified zeaxanthin from these specialty manufacturers, in synthetic racemic mixtures that contain large amounts of the undesirable S-S and S-R isomers, ranges from about $90 to about $125 per milligram (which translates to about $100,000 per gram). Clearly, zeaxanthin is not a widely available chemical, and is not available to the public except in extremely small trace quantities, in mixtures of other carotenoids.

Prior art items which describe zeaxanthin production using microbial fermentation include the following:

(1) Courington and Goodwin 1955, which is the earliest known reference describing the production of zeaxanthin by microbes. The bacteria they described reportedly belonged in the genus Flavobacterium; however, as noted below, microbial classification definitions have changed a great deal over the past few decades, and those bacteria probably would not be classified as Flavobacterium under the current nomenclature.

(2) U.S. Pat. No. 3,891,504 (Schocher and Wiss, 1975, assigned to Hoffman LaRoche). This patent described the production of zeaxanthin by microbes from the genus Flavobacter, which were deposited with the American Type Culture Collection and given ATCC numbers 21081 and 21588. As with the Courington and Goodwin 1955 microbes, these microbes would not be classified as Flavobacter today. These cells and their zeaxanthin pigment were fed to chickens, and caused suitable coloration.

(3) U.S. Pat. No. 3,841,967 (Dasek et al, 1974, assigned to Nestle). This patent described the production of zeaxanthin by microbes from the genus Flavobacter; some of their work involved the same strain cited in the Hoffman-LaRoche U.S. Pat. No. '504 (21081 and 21588), and they also used ATCC strain 11947. This patent, as well as U.S. Pat. No. 3,951,743 (Shepherd et al, 1976, also assigned to Nestle) described certain cell culturing conditions and nutrient media that would be used to increase the quantity of zeaxanthin produced by the cells being cultured.

(4) Two more recent US patents (U.S. Pat. Nos. 5,308,759 and 5,427,783, both invented by Gierhart and assigned to Applied Food Biotechnology, Inc., the same assignee in this current application) describe a strain of bacteria (Flavobacterium multivorum) isolated from a Missouri waterway. These bacteria were discovered to create zeaxanthin without creating substantial quantities of other carotenoids. This is important, because it makes more zeaxanthin available as a pigment, when fed to poultry or fish to give their flesh a darker color. AFB's wild-type strain of F. multivorum was deposited with the ATCC, and was given ATCC accession number 55238. Because these bacteria generate a certain type of lipid called sphingolipids, the ATCC has provisionally reclassified these bacteria as Sphingobacterium multivorum, which is the name they are listed under in the ATCC's catalog. However, as of the filing date of this application, the Sphingobacterium name that appears in the ATCC catalog has not yet appeared in either of the reference works which are widely recognized as the official guides to microbial taxonomy: Bergy's Manual of Systematic Bacteriology, which is appended and updated by the International Journal of Systematic Bacteriology.

Gierhart's U.S. Pat. No. '759 claims methods for producing zeaxanthin, using AFB's F. multivorum bacteria. The U.S. Pat. No. '783 (which was a divisional) claims feed mixtures that can be given to poultry or fish. Both of these patents are limited to using zeaxanthin in poultry or fish feed; although zeaxanthin is much more expensive than lutein, it is several times more effective (on a per-weight basis) than lutein in imparting color to animal flesh or chicken yolks. Neither of the Gierhart patents says or suggests anything about using zeaxanthin for treating humans.

Various efforts to synthesize zeaxanthin by standard chemical means (without using microbial fermentation) have been reported over the past 20 years (e.g., U.S. Pat. No. 4,153,615, Saucy 1979). However, non-fermentation processes suffer from several disadvantages. They typically require numerous reaction steps, and each step has a less-than-100% yield, so that the final yield of zeaxanthin at the end of the multi-step processing tends to be relatively poor. In addition, chemical synthesis tends to yield undesirable S-S and S-R stereoisomers of zeaxanthin, as well as various conversion products such as oxidized zeaxanthin, and zeaxanthin molecules which have lost one or more of the double bonds in the straight portion or end rings.

Recently, Hoffman-LaRoche obtained two US patents which relate to the chemical synthesis of the R-R isomer of zeaxanthin; these are U.S. Pat. Nos. 4,952,716 (Lukac et al 1990) and 5,227,507 (Lukac et al 1993). These processes require the production and purification of three major intermediates, with yields of approximately 70 to 85% for each intermediate from its precursor. The overall process described in the Lukac et al patents apparently requires a series of 14 reaction steps, which take a minimum of 83 hours (excluding purification), and the synthesis reactions yield a mixture of reactants and products. This reaction mixture must then be extensively treated to purify the R-R isomer of zeaxanthin. Accordingly, the entire process that would be required for both synthesis and purification using this technique would make production on a commercial scale very difficult, and extremely expensive.

Two types of poultry feed additives may be of interest, since they have the highest lutein or zeaxanthin quantities of any commercially available animal feeds. Certain types of poultry feed additives prepared from corn gluten contain a relatively high percentage of zeaxanthin (about 15–30%), when measured as a percentage of total carotenoids. However, the total carotenoid content of these feed additives is very low (only about 100 milligrams of total carotenoids per pound of poultry feed). The other type of poultry feed additive is prepared from marigold extracts. This additive contains roughly 100–200 times as much yellow pigment per pound of additive (i.e., about 10 to 20 grams of lutein and zeaxanthin per pound); however, more than 95% of the yellow pigment in this marigold preparation is lutein, not zeaxanthin. Zeaxanthin comprises only about 2 to 5% of the yellow pigment in this poultry feed additive (Bauernfeind 1981).

As a matter of prior art, it should also be noted many health food stores sell carotenoid preparations that are labelled as being beneficial to the eyes and eyesight. That labelling claim on carotenoid mixtures may be valid and reasonable, since (as noted above) β-carotene and vitamin A are known to be useful and beneficial in the eyes as general anti-oxidants. However, even though at least one commercially available carotenoid mixture that is sold in health food stores (the "Beta-Carotene Formula Preparation," sold by General Nutrition Corporation) lists zeaxanthin as one of the carotenoids contained in their carotenoid mixtures, none of the commercially available carotenoid mixtures contains more than extremely small, trace quantities of zeaxanthin. The great majority of the carotenoids in the carotenoid mixtures that are sold in health food stores are other, non-zeaxanthin carotenoids (mainly β-carotene and vitamin A).

The current positions and publicly stated research goals of several government agencies and research consortia are also worth noting. The National Institutes of Health, acting through the National Eye Institute (NEI) and the National Advisory Eye Council, has issued two recent government publications which are directly relevant. These two reports are "Vision Research: A national Plan 1994–1998," NIH Publication No. 93-3186 (1994; see pages 55–65 in particular), written by the members of the National Advisory Eye Council, and "Age related eye disease study," NIH Publication 93-2910 (1993). Both publications, and the research projects they describe, focus on β-carotene rather than zeaxanthin as the compound which holds the greatest apparent promise for treating AMD. To the best of the Applicants' knowledge and belief after discussing the subject with officials of the NEI, neither the NEI nor any other organization affiliated with the National Institutes of Health is willing to fund, or has recently funded, any research on zeaxanthin as a potential treatment for AMD. Instead, the NIH and various other tax-funded organizations are allocating millions of dollars to carry out research on β-carotene as the most promising candidate agent for treating or preventing AMD.

Another research group that deserves attention (and which contains various members who are employed as researchers at the NEI) is the Eye Disease Case Control Study Group. This group recently published two articles entitled, "Antioxidant status and neovascular age-related macular degeneration," Arch. Ophthalmol. 11: 104–109 (1993), and "Risk factors for neovascular age-related macular degeneration," Arch. Ophthalmol. 10: 1701–1708 (1992). As in the official NIH reports, neither of these articles teaches or suggests the use of zeaxanthin as a drug for treating AMD. To the best of the Applicants' knowledge and belief, this consortium also has declined or refused to fund any research into zeaxanthin as a possible agent for treating or preventing AMD.

Accordingly, as of late 1995, there are no available sources of concentrated or purified zeaxanthin for human use, either as a drug or as a nutritional supplement.

One object of this invention is to disclose an economically viable method of producing zeaxanthin pills (such as capsules or coated tablets) which contain the R-R stereoisomer of zeaxanthin as the sole detectable zeaxanthin isomer in the formulation, and which are intended and well-suited for human ingestion as a prescription drug or as a nutritional supplement, to help treat or prevent macular degeneration.

Another object of this invention is to disclose food preparations such as margarine, dairy products, syrup, cookie dough, meat preparations that will not be subjected to harsh cooking conditions, and other similar foodstuffs, which contain the R-R stereoisomer of zeaxanthin as the sole detectable zeaxanthin isomer in the formulation, and which are intended for human ingestion, and which can be produced at a reasonable and economically viable cost in commercial quantities.

Another object of this invention is to disclose zeaxanthin preparations that are intended and well-suited for human ingestion as a prescription drug or nutritional supplement, which contain the R-R stereoisomer of zeaxanthin as the sole zeaxanthin isomer in the formulation, and which do not contain any other carotenoids that would compete against zeaxanthin for alimentary uptake and which would therefore reduce the bioavailability of zeaxanthin if present in a mixed carotenoid preparation containing zeaxanthin and other competing carotenoids.

Another object of this invention is to disclose that zeaxanthin preparations produced by fermenting AFB's strain of F. multivorum (ATCC accession number 55238) or its descendants are exceptionally well suited for human ingestion as a prescription drug or nutritional supplement, for treating or preventing macular degeneration.

Another object of this invention is to disclose that a compound called tertiary butyl hydroquinone, abbreviated as TBHQ and also called 2-(1,1-dimethyl)-1,4-benzenediol, is an especially good stabilizing agent in formulations containing zeaxanthin for human ingestion.

Another object of this invention is to disclose micelle formulations containing the R-R isomer of zeaxanthin, for improved bioavailability.

These and other objects will become more apparent in the following summary and description of the invention.

SUMMARY OF THE INVENTION

This invention discloses zeaxanthin preparations which contain the 3R-3'R stereoisomer of zeaxanthin as a sole detectable isomer, packaged in a form that is intended and suitable for oral ingestion by humans as a therapeutic drug or nutritional supplement. Zeaxanthin is a yellow carotenoid pigment found in the macula (in the center of the human retina), which helps protect retinal cells against phototoxic damage. The pure R-R stereoisomer can be prepared by fermenting cells, such as Flavobacterium multivorum (ATCC 55238), which do not create any detectable quantity of the undesirable S-S or S-R isomers, and which do not synthesize any other carotenoids. The R-R isomer can be concentrated, in large quantities and at low cost, into a viscous oily fluid containing about 5 to 20% zeaxanthin, by means of a simple solvent extraction process. This oily fluid can be mixed with a carrier such as vegetable oil and enclosed within a digestible capsule, comparable to a conventional capsule containing Vitamin E. Alternately, a zeaxanthin fluid can be added to various types of foods, such as margarine, dairy products, syrup, cookie dough, and certain types of meat preparations which are not subjected to harsh cooking. Additional purification steps can also be used to purify zeaxanthin to a granular or powdered state which contains nearly pure zeaxanthin. Such processing can be used to create formulations such as ingestible tablets, and particulate formulations that can be added to soups, salads, drinks, or other foods. Preferred stabilizers and anti-oxidants are also disclosed herein. When consumed by humans in any of these modes, the pure R-R stereoisomer of zeaxanthin can help treat and prevent macular degeneration, one of the leading causes of blindness and vision loss, especially among the elderly.

DESCRIPTION OF THE PREFERRED EMBODIMENTS

This invention discloses formulations of zeaxanthin which are designed and intended for oral ingestion by humans as therapeutic drugs or nutritional supplements, and which contain the 3R-3'R stereoisomer (also referred to as the R-R isomer, for convenience) as the sole detectable isomer of zeaxanthin. These formulations can be used to treat, retard, or prevent macular degeneration in humans.

As mentioned above, methods of synthesizing and purifying the R-R isomer of Zeaxanthin are disclosed in a co-filed related application, Ser. No. 08/551,166, the teachings of which have already been incorporated herein by reference.

Figure 1:
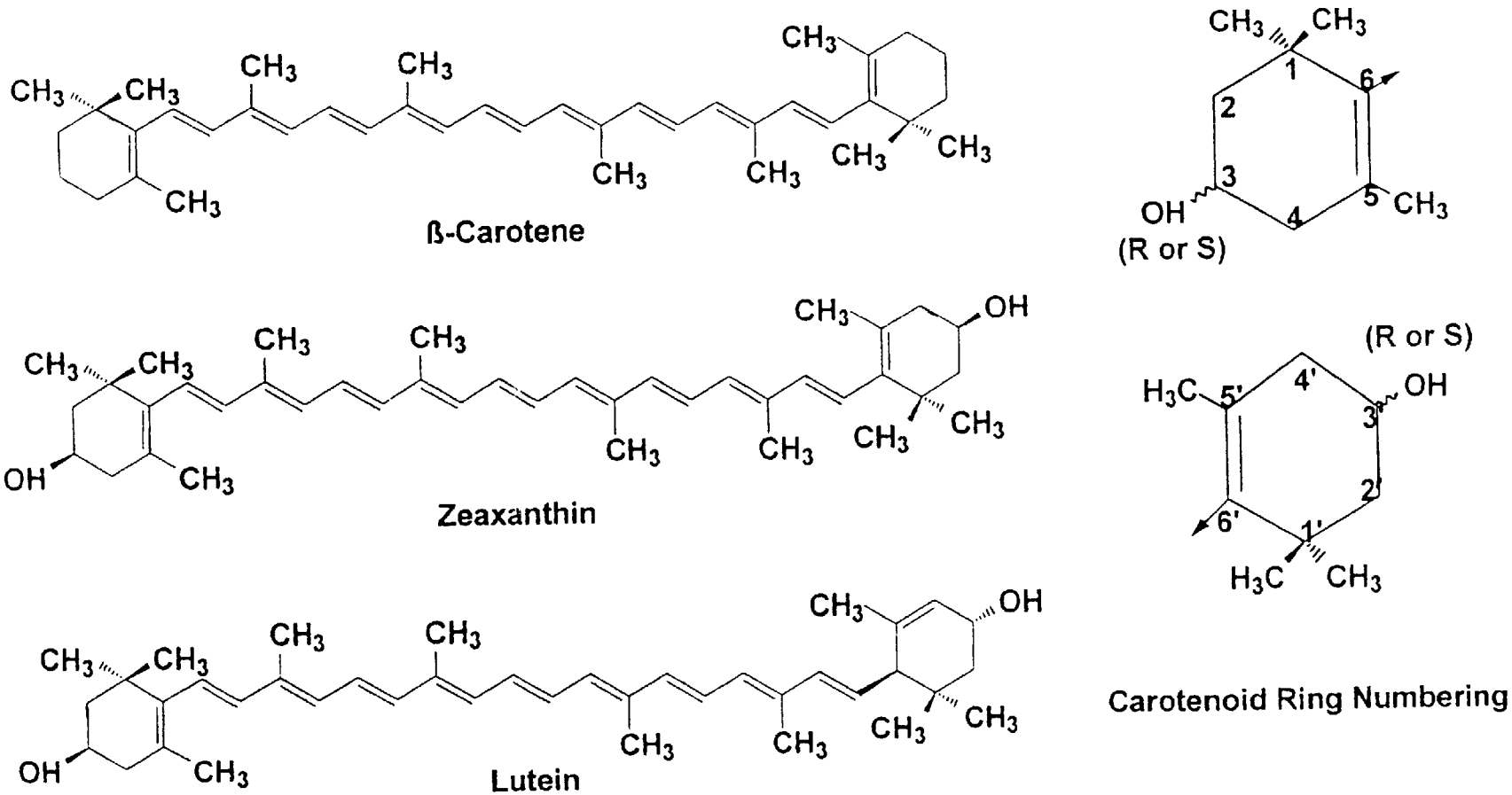
FIG. 1 is a depiction of the chemical structures of three closely-related carotenoids (beta-carotene, lutein, and zeaxanthin), showing the fully-conjugated structure of zeaxanthin and the numbering system for both end rings. These chemical structures are known in the prior art.
Figure 2:
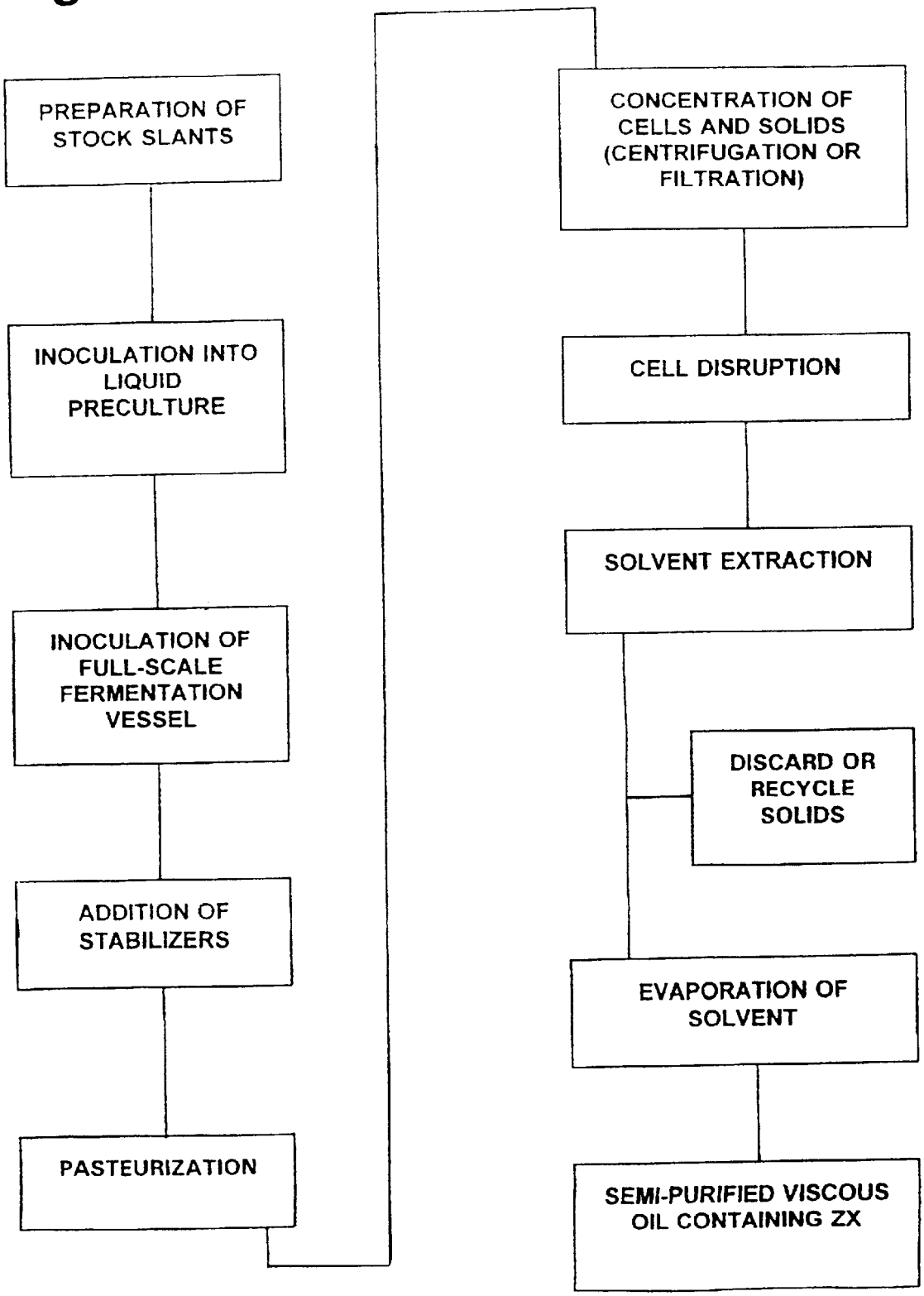
FIG. 2 comprises a flow chart which describes the primary steps in purifying zeaxanthin generated by microbes that synthesize a stereoisomerically pure form of 3R-3'R zeaxanthin.

To briefly summarize some of the main teachings of that application, a preferred method of synthesizing a pure form of the R-R isomer of zeaxanthin involves fermenting bacterial cells descended from a strain of Flavobacterium multivorum bacteria (ATCC number 55238; referred to in the ATCC catalog as Sphingobacterium multivorum, although that name has not yet appeared in the Bergy's Manual of Systematic Bacteriology or the International Journal of Systematic Bacteriology). These cells, and their isolation, are described in U.S. Pat. Nos. 5,308,759 and 5,427,783 (Gierhart; assigned to Applied Food Biotechnology, Inc., the same assignee in this current application). After its discovery and isolation, this bacterial strain was found to synthesize zeaxanthin as a sole or predominant carotenoid; under proper fermentation conditions, it synthesizes virtually no substantial quantities of other carotenoids. Therefore, the extremely difficult chore of purifying zeaxanthin by separating it from other closely related carotenoids (such as lutein or β-carotene, shown in FIG. 1) can be completely avoided if this bacterial strain or its descendants are used.

As described in Example 4, it also has recently been determined that this F. multivorum strain synthesizes the R-R isomer of zeaxanthin as a sole detectable stereoisomer. Therefore, the chore of trying to separate the R-R isomer from other stereoisomers of zeaxanthin, which is effectively impossible when commercial quantities are involved, can also be completely avoided.

Example 1, below, describes the preferred nutrients and methods that can be used to generate large commercial quantities of the R-R isomer of zeaxanthin, by fermenting F. multivorum (ATCC 55238). As known to those skilled in the art, nutrients and methods which are used to cultivate bacteria in small-scale laboratory tests often become unduly expensive and difficult to monitor and control when an effort is made to convert them into large-scale commercial fermentation operations. Accordingly, the Applicants have invested substantial time and expertise in developing and testing nutrients and culture conditions for use with its F. multivorum strains which are less expensive and substantially easier to work with than the lab-scale fermentations disclosed in U.S. Pat. Nos. 5,308,759 and 5,427,783.

By way of illustration, the best lab-scale nutrient media disclosed in U.S. Pat. Nos. 5,308,759 and 5,427,783 contained corn flour (a granular powder that is difficult to work with), amylase and glucoamylase (to help digest the corn flour), lipase, and thiamine. During subsequent research to develop scale up the fermentations to commercial quantities, different culture media were developed by the Applicants which provide even better yields of zeaxanthin while requiring no corn flour, amylase, glucoamylase, lipase, or thiamine. The preferred commercial-scale fermentation media and methods disclosed in Example 1 can be sealed up to virtually any desired volume, and they will cause the F. multivorum strain isolated by the Applicants to generate large quantities of R-R zeaxanthin. Most of the zeaxanthin remains inside the cells and is effectively bound to the cell membranes.

Example 2 discloses methods for adding one or more stabilizing agents, to protect the zeaxanthin against oxidation, decomposition, isomeric rearrangement, and other types of degradation as the bacterial cells are killed and processed. Various candidate stabilizing agents have been tested by the Applicants, and the best results obtained to date have used a combination of four agents: tertiary butyl hydroquinone (TBHQ, also called 2-(1,1-dimethyl)-1,4-benzenediol), ethoxyquin, tocopherol, and ethylenediamine-tetraacetate (EDTA).

Example 3 discloses a series of steps that can be used to remove and partially purify the zeaxanthin from the bacteria. These steps can be broken down into four main processes: (1) killing the bacterial cells, using means such as heat (pasteurization); (2) breaking the bacterial cells apart by rupturing their cell membranes, to render the zeaxanthin more accessible; (3) removing the zeaxanthin from the cell and nutrient solids, by using a solvent-extraction process; and (4) evaporating the solvent, which leaves behind an oily mass that contains partially-purified zeaxanthin.

Example 4 describes a method that was used to purify the R-R isomer of zeaxanthin to about 98% purity, in powdered form.

Example 5 describes the use of bile salts such as glycocholate salts or taurocholatete salts which, when homogenized with zeaxanthin, create micelles which may help protect the zeaxanthin from acids in the stomach and also greatly enhance biological absorption through the small intestine.

Examples 6 and 7 describe in vivo retinal tests on Japanese quail, which provide a good animal model for the human macula.

*Periodic oral ingestion is the preferred mode of administering zeaxanthin for retinal protection purposes, using ingestion modes such as daily or weekly capsules, or occasional use of zeaxanthin-supplemented food preparations such as margarine. "Periodic" ingestion does not require regular ingestion at fixed intervals (such as daily or weekly pills), but instead refers to occasional, intermittent ingestion which allows a reasonable period of time to elapse between dosages, thereby allowing appropriate and gradual deposition of small quantities of zeaxanthin in the macular tissue. As with any vitamin supplement, a single dosage may be beneficial, but a single dosage will not be as beneficial over a period of years as periodic ingestion of appropriate small dosages. Pharmacodynamic studies on carotenoid uptake in humans and test animals suggest that daily ingestion is preferable to weekly or other sporadic intake, due to "loading" factors that are manifested in blood concentrations.*

*This invention also discloses a method of creating zeaxanthin preparations that contain the R-R isomer of zeaxan-*

*thin as a heavily dominant (or sole detectable) carotenoid. Unlike most bacterial strains, the F. multivorum cells described herein do not generate a mixture of carotenoids; instead, this bacterial strain generates the R-R isomer of zeaxanthin as a sole detectable carotenoid. Since zeaxanthin must compete against other carotenoids (including dietary carotenoids) for alimentary uptake and tissue deposition, this is highly useful for increasing zeaxanthin uptake and retinal deposition after oral administration, especially when zeaxanthin is being used as a drug to treat diagnosed cases of macular degeneration.*

Preferred Forms for Human Ingestion

The foregoing narrative and Examples 1–3 describe a procedure for synthesizing and semi-purifying zeaxanthin to a point which provides a viscous, oily, hydrophobic fluid that contains the R-R isomer of zeaxanthin with little or no other carotenoids, and with no significant quantity of the undesired S-S or S-R isomers of zeaxanthin. This fluid, if packaged or mixed into forms that are suitable for ingestion by humans, can be directly ingested by humans to provide a therapeutic or nutritional supply of the R-R isomer of zeaxanthin, without requiring further purification of the R-R zeaxanthin to a point of crystallization.

A variety of suitable modes of packaging for human ingestion can be used and provided, so long as any such packaging protects the zeaxanthin from oxidation and takes proper account of the hydrophobic nature of the zeaxanthin-containing fluid.

One preferred mode of packaging and delivery for human ingestion comprises (1) mixing the oily zeaxanthin-containing fluid with a suitable hydrophobic fluid (such as vegetable oil) that can serve as a diluent, carrier, and anti-oxidant, and (2) emplacing the oily mixture inside a closed digestible capsule. Such capsules can be made of rigid or stiff material if desired; alternately, they can be made of pliable material, as commonly used in capsules containing vitamin E. If the enclosing capsule is made of material which can withstand the acidity of the stomach and be digested by enzymes after it enters the intestines, the zeaxanthin can be protected against acidic modification or degradation inside the stomach, and the bioavailability of the zeaxanthin can be increased somewhat; however, it is known that at least a portion of the zeaxanthin that enters the stomach as a constituent of chewed vegetable mass is able to pass through the stomach unharmed, so it is not essential to protect zeaxanthin from stomach acidity. Accordingly, since effectively unlimited quantities of R-R zeaxanthin can be produced using microbial fermentation as described herein, the choice of preferred capsule material will be an economic preference rather than a scientific imperative.

An alternate form of packaging for human ingestion can utilize tablets rather than capsules, provided that a solid binder material is used which will hold the tablet together after manufacture using suitable pressure. If desired, such tablets can be coated with any suitable coating, such as an enteric coating which remains intact until after the tablet passes through the stomach and enters the intestines. Zeaxanthin is believed to be susceptible to degradation at high pressures. Accordingly, it is assumed that compressed tablets will be somewhat less preferred than capsules. However, various tablet binder materials and coatings are known which can be used to minimize the pressures necessary to ensure tablet cohesion, so compressed tablets can be used as a mode of ingestion, if desired.

Other suitable forms of packaging for human ingestion can utilize the oily semi-purified zeaxanthin fluid as an additive in a suitable type of food or food ingredient. Zeaxanthin is a yellow-orange pigment with the same generally hydrophobic characteristics as vegetable oil, shortening, chicken fat, and other carotenoid food colorings which are widely used, such as β-carotene. Accordingly, it can be added as a nutritious coloring agent to a wide variety of suitable foods, including margarine, dairy products (such as butter, cheese, or yogurt), syrup, cookie or brownie dough, baked foods such as brownies or cookies, soup ingredients (either in dried form such as bouillon cubes or powders, or in hydrated form such as in canned soup). If used in meat preparations, such preparations preferably should be packaged and suited for consumption without heating, such as luncheon meat, or for relatively mild microwave-type heating rather than frying or broiling, such as hot dogs.

The foregoing are examples of several conventional forms of packaging for human ingestion. Other forms of packaging are also feasible, and may be preferred for various uses, or by certain consumers. There is a substantial body of published articles and patents relating to the formulation and use of β-carotene and other carotenoids as food colorings and nutritional additives. Such publications include, for example, Klaui et al 1970; Klaui and Bauernfeind 1981; Colombo and Gerber 1991, while relevant US patents include U.S. Pat. Nos. 4,522,743 (Horn et al 1985), 5,180,747 (Matsuda et al 1993), 5,350,773 (Schweikert et al 1994), and 5,356,636 (Schneider et al 1994). Due to their very close chemical similarities and physical properties, any technique, additive, stabilizer, or other method for adding β-carotene or lutein to any type of food intended for human ingestion is also likely to be directly applicable to the R-R isomer of zeaxanthin. This can be evaluated, for any particular type of food or method of preparation, using no more than routine experimentation.

Some of the alternate forms of packaging which can be used with R-R isomer of zeaxanthin may involve purifying the zeaxanthin to a state which is more highly purified than the type of oily fluid that can be generated using solvent extraction as described in Example 3. For example, an oily fluid generated by solvent extraction can be further purified by means such as (1) two-solvent systems which use a combination of two selected solvents; (2) crystallization or adsorption on a substrate (such as a woven filter bed) that encourages crystallization of zeaxanthin; or (3) other processing techniques such as counter-current chromatography.

If desired, the R-R isomer of zeaxanthin can be purified to a point where it will crystallize as a pure or almost-pure solid, using methods such as described in Colombo and Gerber 1991, which describes crystallization of pure β-carotene. Although this level of purification is very expensive, it is technically possible, using known techniques. If a crystallized or other highly purified form of zeaxanthin is preferable for a specific intended use, its suitability for such use in commercial-scale preparations will be a question of economics rather than technical feasibility.

Zeaxanthin can also be mixed and treated with the various ingredients and methods described in U.S. Pat. No. 5,356,636 (Schneider et al 1994) to form a granular formulation which is stabilized and protected against oxidation. Such granular zeaxanthin preparations can be packaged and used in, for example, flavoring mixtures that also contain salt or other spices for use in flavoring foods such as soups, salads, popcorn, casseroles, etc., baking mixes for use in preparing cakes, cookies, brownies, etc., dried soup mixes, additives for milk such as chocolate-flavored powders, and other granular formulations. As used herein, "granular formulations" includes any pourable composition composed of distinct particles less than roughly 0.5 centimeter (¼ inch) in diameter. Examples include fine-grained powders, comparable to flour or cake mix; formulations with intermediate-sized grains, comparable to salt or sugar; and large-grained formulations, comparable to freeze-dried instant coffee.

Biological absorption of granular hydrophobic compounds increases substantially when granular particle sizes are kept as small as possible. Therefore, various methods that have been developed for microencapsulating fatty compounds, and for creating stabilized fine powders and microscopic "beadlets" containing fatty compounds, will be of particular interest in creating fine-grained zeaxanthin powders and other formulations. Methods and reagents for creating very small particles which are coating by materials that help protect the enclosed compound from degradation by stomach acid are described in various items of prior art, including Klaui and Bauernfeind 1981, Colombo and Gerber 1991, and U.S. Pat. Nos. 4,522,743 (Horn et al 1985), and 5,356,636 (Schneider et al 1994).

In addition, methods have also been developed for creating carotenoid-containing "micelles" which are less than 1 micron in diameter, using certain types of bile salts (see Olson 1994). As described in Example 5, the oily fluid which contains R-R zeaxanthin can be mixed with suitable bile salts and other salts, and processed in a mechanical homogenizer, to create such micelles. These can then be diluted (if desired) to any desired concentration using a carrier or diluent fluid such as vegetable oil, and the mixture can be enclosed within a capsule that will protect the micelles against degradation by stomach acid. Olson 1994 indicates that this type of micelle formulation can greatly increase absorption of carotenoids in the human body.

Purification techniques for lutein, a closely related and chemically similar carotenoid, are disclosed in U.S. Pat. No. 5,382,714 (Khachik 1995). This system used a cold ethanol/waster system in a two-solvent extraction system, followed by lyophilization, to purify lutein. U.S. Pat. No. 4,851,339 (Hills 1989) also described purification of carotenoids from algae.

Since the quantities of unwanted luteins or other competing carotenoids generated by the F. multivorum strain described herein are very low, nearly any chemical purification technique which has been developed for lutein or any other carotenoid can be carried out on the zeaxanthin mixtures generated by the F. multivorum strain, and it is likely to give good results due to the close chemical similarities between zeaxanthin and other carotenoids. The efficacy and suitability of any known purification technique developed for any carotenoid can be evaluated for zeaxanthin preparations as descried herein, using no more than routine experimentation.

In the opposite direction (i.e., using fewer purification steps and stopping short of creating the semi-pure oily liquid described in Example 3), it may be possible to add intact F. multivorum cells containing zeaxanthin directly to one or more foods intended for human consumption. Numerous human foods (including cheese, yogurt, beer, and certain types of milk that have had acidophilus bacteria or other microbes added) contain intact microbial cells, and there is no known pathogenicity associated with the F. multivorum cells isolated by Applied Food Biotechnology, Inc. These cells are gram-negative bacteria, and do not have the cell wall structures that characterize gram-positive bacteria. In addition, since they were isolated from a relatively cold artesian waterway, they are adapted to living in cold water and cannot survive or reproduce well at temperatures inside the human body. When fed directly to animals such as poultry and fish, these cells apparently are well-suited as delivery vehicles for zeaxanthin; after ingestion, the zeaxanthin is released when the cells are digested, absorbed into the bloodstream through the intestinal walls, and deposited into various animal tissues at expected and appropriate locations. Accordingly, intact F. multivorum cells containing the R-R stereoisomer of zeaxanthin, and which can be killed by a process such as pasteurization if desired, may be suitable for direct human consumption, if desired, in a suitable carrier substance such as yogurt, cheese, milk, or beer.

Alternately, various other types of microbial cells (such as certain types of yeast) which are well-suited for human consumption can be genetically transformed with genes which encode enzymes that will synthesize zeaxanthin in the transformed host cells. Such zeaxanthin-producing genes can be isolated from the F. multivorum cells described herein, or from other known microbial sources, such as the microbial "crt" genes described in U.S. Pat. No. 5,429,939 (Misawa et al 1995).

Use of Zeaxanthin as a Drug to Treat Macular Degeneration

As discussed in the Background section, the various forms of macular degeneration can be diagnosed by ophthalmologists, using specialized retinal photography to evaluate the amount of soft (wet) drusen and/or lipofuscin in or behind the retina, supplemented by other diagnostic techniques known to those skilled in ophthalmology. Such tests are most commonly carried out when relatively simple eyesight tests indicate a significant loss of peripheral vision.

If a patient has been diagnosed as suffering from macular degeneration, then an ophthalmologist or other physician can prescribe administration of the R-R isomer of zeaxanthin to the patient as a drug to treat the condition. As used herein, "treatment" of macular degeneration by means of administering zeaxanthin includes any effort intended to reduce, prevent, or delay subsequent or additional degeneration of the macula.

The "dry" form of age-related macular degeneration (i.e., the form which does not involve aggressive capillary growth into the retina) is of primary interest herein, since most cases of dry AMD are likely to involve an inadequate supply of zeaxanthin (a protective agent) in the macular as one of the etiological agents of this class of macular degeneration. Indeed, a deficit of zeaxanthin in the macula, coupled with high levels of exposure to direct sunlight may well be the two primary causes of AMD. These may work in combination with each other to generate (or greatly aggravate) AMD in patients who are subjected to both causative agents.

However, even though dry AMD is the type of macular degeneration that is of dominant interest herein, it is also recognized and anticipated that the R-R isomer of zeaxanthin will also be prescribed and used (or at least tested) as a treatment for any and all types of macular degeneration.

There are two major reasons why zeaxanthin will be prescribed and used as a potential treatment for other types of macular degeneration. First, with the exception of a broad claim that carotenoid mixtures (mainly β-carotene and Vitamin A) might be generally beneficial to the eyes and eyesight, no other treatments are known to be effective in stopping the advancing retinal damage caused by macular degeneration, including the wet form of macular degeneration caused by aggressive capillary growth into the retina. Laser ablation of encroaching capillaries is the best treatment currently known for fighting wet macular degeneration; however, it is not a permanent cure, and it can only stave off blindness for a limited time.

Since no other treatments which are truly effective in stopping macular degeneration are available, then any agent that can be used effectively to stop the encroaching damage caused by any type of macular degeneration will (and should) be carefully tested and evaluated. Zeaxanthin emphatically falls within the category of a highly promising treatment, and it should and will be tested to see whether it can help reduce, retard or even reverse the damage caused by any and all forms of macular degeneration.

And second, zeaxanthin acts as a protective agent in the retina. It provides a mechanism for safety absorbing and handling excess light energy in the blue and near-ultraviolet range; in this manner it, prevents "phototoxic" damage to retinal cells and photoreceptors. Even if an unrelated etiologic agent (such as aggressive capillary growth) is the immediate or initial cause of damage in a patient, any type of secondary damaging agent will cause even more damage in a system that is being subjected to high levels of stress and disruption. Accordingly, a simple and convenient treatment that can help restore or supplement the concentration of a protective agent inside a retina which is under attack is likely to help promote and enhance the retina's ability to sustain its natural and proper homeostasis and defend itself against the attack.

Accordingly, this invention discloses a method of increasing the concentration of a natural and beneficial protective agent in the retinas of patients diagnosed as suffering from macular degeneration, to help protect and defend the macula and to help it sustain its desired homeostasis, regardless of the specific etiologic agent which is causing the degeneration in a specific patient, and regardless of the particular type of macular degeneration which is occurring in the eyes of a specific patient.

Furthermore, as a protective agent, the R-R isomer of zeaxanthin can help provide a beneficial effect at any stage of macular degeneration, provided that total blindness has not yet occurred and some portion of the retina remains functional. Accordingly, the R-R isomer zeaxanthin treatment described herein can be used to treat patients suffering from early-onset, moderate, or advanced macular degeneration.

It is not claimed that the R-R isomer zeaxanthin treatment described herein will offer a "cure" for macular degeneration. This treatment is not expected to reverse retinal damage that has already occurred, or to restore damaged retinal tissue to a pristine condition. Similarly, it is not expected to completely halt the advancing encroachment of macular degeneration in all patients, or even in any patients. Nevertheless, it still offers a highly useful and beneficial treatment for macular degeneration, in the form of a drug that can slow down and retard the encroachment of additional retinal degeneration.

*To be effective as a prescription drug for patients suffering from macular degeneration, a zeaxanthin preparation as described herein must have a sufficient amount of the R-R isomer of zeaxanthin to rise to the level of a therapeutic agent. To achieve this level of therapeutic benefit, the zeaxanthin preparation must contain more than merely trace quantities of zeaxanthin, which are present in various mixed-carotenoid powders sold in health food stores. Formulations in capsule, tablet, or powdered form intended for use as a prescription drug should contain the R-R isomer of zeaxanthin at a concentration of at least about 2 percent, by weight. Expressed as absolute weight rather than a percentage, preparations intended for use as a therapeutic drug in patients suffering from macular degeneration preferably should contain at least about 3 milligrams of the R-R isomer of zeaxanthin, per dosage. Ingestible capsules containing up to about 25 milligrams (or any lesser quantity) can be created in a highly economical manner, using a single-step solvent extraction as described below. Capsules or powders containing higher quantities (such as 100 milligrams or more) can be created using more extensive zeaxanthin purification methods, such as the methods described in Example 4.*

Use of Zeaxanthin as a Vitamin or Nutritional Supplement

It is also recognized and anticipated by the Applicants that the isomerically pure R-R form of zeaxanthin can (and should) be used as a nutritional supplement, in formulations comparable to vitamin pills or as an additive in suitable foods such as margarine, which will be ingested by people who have not been diagnosed as suffering from AMD but who are concerned about protecting their eyesight over the long term.

*When ingested for such purposes, appropriate dosages must be substantially higher than the trace quantities found in powders that are sold in health food stores today, but they will be substantially lower than when zeaxanthin is used as a therapeutic drug. Although preferred dosages for use as vitamin or nutrition supplements or food additives will need to be determined through human clinical studies, it is anticipated that such dosages are likely to be in the range of about 0.5 to 25 milligrams for a dosage to be ingested on a daily basis.*

Dietary supplements containing the R-R isomer of zeaxanthin (in pills, capsules, powders, syrups, etc.) are likely to be widely recommended to the interested public by physicians and other health care professionals, and by government, educational, insurance, and other organizations and publications interested in public health and in preventing blindness.

EXAMPLES

Example 1

Commercial-Scale Fermentation

The nutrient medium that was preferred by the Applicants for lab-scale testing of F. multivorum was identified as nutrient medium E under Example 3 in U.S. Pat. Nos. 5,308,759 (Gierhart 1994) and 5,427,783 (Gierhart 1995). This lab-scale medium contained several ingredients that were expensive and difficult to work with, and substantial work to create a better commercial-scale nutrient medium was carried out after the initial filing date of those applications. The nutrient media that are currently preferred for commercial-scale fermentation have eliminated corn flour and several other ingredients, and contain either high maltose corn syrup of sugar beet molasses at concentrations ranging from 1 to 10% w/v, along with corn steep liquor at 0.5 to 4% w/v; ammonium sulfate heptahydrate at 0.5% w/v; sodium chloride at 0.5% w/v; magnesium sulfate heptahydrate at 0.1% w/v; sodium acetate at 0.1% w/v; ferrous sulfate heptahydrate at 0.001% w/v; yeast extract at 0.2% w/v; thiamine-HCl at 0.01% w/v; between 1 and 6% w/v hydrolyzed casein (such as NZ Amine HD, sold by Sheffield Products, Division of Quest International, Norwich, N.Y.); and vegetable oil at 1% v/v.

After these ingredients are mixed together, sufficient NaOH is added to raise the pH to 6.5; by contrast, when the nutrient medium was adjusted to pH 7.5, as described in the lab-scale experiments in U.S. Pat. Nos. 5,308,759 and 5,427,783, too many solids precipitated out from the corn steep liquor.

The culture medium is sterilized by autoclaving at 121° C. for 30 minutes, then it is cooled to 27° C. and inoculated with 5 to 10% v/v of a "liquid preculture" containing a strain of F. multivorum which produces the R-R isomer of zeaxanthin without producing S-S or S-R isomers of zeaxanthin, and without producing any other carotenoids in significant quantities.

The cells used to prepare a liquid preculture are maintained on a slant tube of plate count agar. These slant cultures are inoculated with clonal colonies of F. multivorum descended from the strain deposited by the Applicants with the ATCC, and given ATCC accession number 55238. After incubation for 48 hours at 28° C., stock slants are refrigerated at 4° C. until use as inoculum for liquid media. Viable cells can also be frozen using conventional freezers, dry ice, or liquid nitrogen, for prolonged storage.

A liquid preculture is prepared using cells taken from an agar slant to inoculate 30 mL of liquid media prepared as described above, contained in a 300 mL baffled flask. The growth conditions are 28° C. at pH 7.2 to 7.6, aerated by agitation at 250 RPM and cultivated for 24 hours. After an initial 24 hour incubation, the cells contained in one or more 30 mL preculture flasks are used to inoculate a ten-fold greater quantity of nutrient medium in a suitably sized fermentation vessel. The cells are then incubated for 48 to 72 hours at 28° C. The pH is maintained between 6.80 and 7.20 using NaOH and/or phosphoric acid. The dissolved oxygen level is kept at 30 to 40% of saturation by bubbling filtered air through the vessel at a rate of 1 volume of air per one volume of liquid per minute while agitating the vessel at 400 to 1000 RPM. Tests using periodic sampling and high performance liquid chromatography have indicated that maximum quantities of zeaxanthin will usually be produced within about 72 hours when the cells are fermented under these conditions.

Example 2

Addition of Stabilizing Agents

Zeaxanthin produced by the fermentation processes of Example 1 needs to be stabilized in order to facilitate subsequent purification and formulation, and to ensure purity. Stabilizing compounds can be added to the F. multivorum cells (or to a cellular extract containing zeaxanthin) at any time during a preparation or purification process; in general, one or more initial stabilizers should be added to the cells while they are still in the fermentation vessel.

Various candidate stabilizers have been tested by the Applicants. The best results obtained to date have used a combination of stabilizing agents, which are mixed together in a small quantity of a suitable solvent (such as about 2 milliliters of ethanol for a 20 liter fermentation vessel) before being added to the cells. The preferred stabilizer mixture contains tertiary butyl hydroquinone (abbreviated as TBHQ; also called 2-(1,1-dimethyl)-1,4-benzenediol) at a quantity which will generate a final concentration ranging from about 250 μg/L up to about 50 mg/L after being mixed with the cells; ethoxyquin at a post-mixing concentration ranging from about 250 μg/L to about 250 μg/L; α-tocopherol at a concentration ranging from about 250 μg/L to about 250 mg/L; and EDTA (ethylene diamine tetra acetic acid) at a concentration ranging from about 500 μg/L to about 500 mg/L. Suitable concentrations can vary widely, and will depend on various factors such as subsequent purification steps and the intended mode of packaging and ingestion. Preferred concentrations for single-pass THF extraction followed by mixing with vegetable oil and water-tight encapsulation in a vitamin-type pill are about 25 to 50 mg/L for TBHQ; 250 to 500 μg/L for ethoxyquin, 250 to 500 μg/L for α-tocopherol; and 500 to 1000 μg/L for EDTA.

After the stabilizing compounds are added, the cell culture is pasteurized by heating to 55° C. for 25 to 50 minutes. This kills the bacterial cells without damaging the zeaxanthin they have produced. The culture is then cooled to room temperature, and the zeaxanthin-containing cells and other solids present in the culture broth are separated from the liquid phase by means of a cross-flow microfiltration system which increases the cells/solids concentration from an initial value of about 10 to 15%, to a filtered concentration of about 60 to 80%, by volume. This procedure results in a cell paste, which also contains some residual solids from the nutrient medium.

For zeaxanthin preparations that are fed to Japanese quail for retinal testing, as described in Examples 6 and 7, the cell paste is frozen to −70° C., then dried by lyophilization at 25° C. at full vacuum, to create a dried biomass containing about 1 to 10% zeaxanthin by weight. In past tests, the quantity of zeaxanthin in each batch was individually measured, and batches having different concentrations were combined and mixed together to ensure consistent concentrations for the Japanese quail tests. To create zeaxanthin preparations for human ingestion, solvent extraction is used to generate a viscous oily fluid as described in Example 3.

Example 3

Semi-Purification into an Oily Liquid

After a cell paste has been created as described in Example 2, it can be treated in any of a variety of ways. As mentioned in the Description of the Preferred Embodiments, the cell membranes can be disrupted if desired, to break open the cells and render the zeaxanthin more accessible, by means such as sonication (high-frequency sound waves), high pressure, or grinding, keeping the temperature of the cells below about 30° C. to prevent oxidation. However, this step has not been necessary when tetrahydrofuran (THF) is used in a solvent extraction step, since THF is quite effective in disrupting the cell membranes without mechanical assistance. Stirring has not been necessary when THF is used in lab-scale operation; however it is likely that stirring during the solvent mixing step would probably be beneficial in commercial-scale operations.

In tests done to date, THF extraction involved mixing about 8 to 20 volumes of purified filtered THF with a volume of cell paste containing 60–80% solids, at a temperature below 25° C., for a period of 2 to 24 hours. The THF aggressively attacks the cells, creating a liquid fraction with what is, in essence, a suspension of flocculent solids in the liquid. The majority of the THF is removed by decanting, which can follow centrifugation at up to 20,000 gravities for several minutes. The THF that remains after decanting can be evaporated at room temperature under full vacuum, to leave behind a viscous oily mass which usually contains about 10% zeaxanthin by weight. Zeaxanthin content in the oily fluid has ranged from about 5 to 20% zeaxanthin, when cell pastes containing 1 to 3% zeaxanthin are treated by THF extraction in a single-pass operation.

Example 4

Preparation of Highly Purified Zeaxanthin in Dry Powdered Form, with 100% Pure R-R Isomer A highly purified zeaxanthin preparation in dry powdered form was created by processing the THF-extracted oily fluid described in Example 3 by means of liquid chromatography, as follows. The oily ZX-containing liquid was dissolved in hexane, and then passed through a chromatography column containing neutral alumina powder. Two column-volumes of hexane were used to wash the column, to remove carotenoid impurities such as β-carotene and lycopene, as well as lipids and other contaminants. A mixture of hexane:acetone at 80:20 was then passed through the column, to release the zeaxanthin. The dissolved zeaxanthin which emerged was collected and dried under vacuum. Chromatographic analysis of the fresh preparation indicated that it was at least 98% pure zeaxanthin; only trace quantities of any impurities were detectable.

After roughly six months of storage in a relatively unprotected state (usually under normal refrigeration with moderately frequent removal; without containing any antioxidants, and without taking any precautions to prevent contact by atmospheric oxygen), a sample of the zeaxanthin preparation was sent for stereoisomeric analysis to Prof. John Landrum (co-author of the Bone, Landrum, et al papers) at Florida International University in Miami. His analysis, using chiral column chromatography with dicarbamate derivatization, indicated that the six-month-old unprotected preparation contained 92% zeaxanthin. The impurities appeared to be mainly keto-carotenoids which pre-eluted before the zeaxanthin; keto-carotenoids have an extra oxygen atom attached somewhere to a carotenoid, and they are common by-products that arise when carotenoids are stored without being protected against oxidation.

Prof. Landrum's chiral analysis indicated that 100% of the zeaxanthin in the preparation was the desired R-R isomer. There were no detectable quantities of the undesired S-S or S-R isomers of zeaxanthin.

It is recognized that chromatography purification as described above, although entirely feasible and highly effective, is not ideally suited to preparing highly purified zeaxanthin to commercial quantities. An alternate method that was developed to purify lutein, described in U.S. Pat. No. 5,382,714 (Khachik 1995; also see Khachik et al 1991), which uses a cold ethanol-water mixture in a two-solvent extraction system, followed by lyophilization, offers a good candidate for evaluation for commercial preparation.

Example 5

Formation of Absorption Enhancers

Zeaxanthin-containing "micelles" which are less than 1 micron in diameter, and which contain only the desired R-R isomer of zeaxanthin, can be obtained from either the solvent extract of biomass or the oily fluid described in Example 3, by using certain types of bile salts, as described in Olson 1994. An oily fluid which contains R-R zeaxanthin can be mixed with a suitable bile salt, such as the phosphate salts of glyco- or taurocholate sold by Marcor Development Company of Hackensack, N.J. or by use of gall bladder extracts containing mixtures of bile salts such as that sold by Salzman Corporation of Davenport, Iowa. This bile material can be mixed with either the solvent extract or oily mass and with certain other salts including sodium chloride, calcium chloride or potassium chloride. This mixture is then processed in a mechanical homogenizer which contains mixing devices such as rotating blades, at a rotation speed and for a duration which can be optimized by routine experimentation, by analyzing the micelle size ranges created by various combinations of blade sizes and shapes, rotation speed, and duration. The resulting micelles are dried free of solvent, if necessary, then diluted to any desired concentration using a carrier or diluent fluid such as vegetable oil. This mixture can then be enclosed within a capsule or other device that will aid in swallowing and help protect the resultant micelles against degradation by stomach acid.

Similarly, other emulsifiers and lipids can be utilized to form emulsions with small particle sizes. Nonionic detergents such as Tweens and Spans can be utilized as per Olson 1994, as well as specifically lipid materials such as phospholipids and sphingolipids, which would form lipid vesicles of small (less than 1 micron) size.

Example 6

Tests of Zeaxanthin on Japanese Quail, Using Different Dietary Groups

All tests involving Japanese quail are being carried out at the Schepens Eye Research Institute of Harvard Medical School (Boston, Mass.), under a contract with Applied Food Biotechnology, Inc. All treatment or control groups contain statistically significant numbers of birds. In most cases, control population groups are the same size as treatment population groups.

All carotenoid-deficient bird feeds are obtained from Purina Mills (St. Louis Mo.). These bird feeds are sold for experimental use only, and are obtained by using grain (such as milo seeds) that is naturally devoid of carotenoids.

All zeaxanthin preparations which are fed to the Japanese quail are in the form of dried biomass from F. multivorum cells that are fermented, stabilized with the agents described in Example 2, pasteurized to kill the cells, and dried using spray-drying. All of these preparative steps are carried out by Applied Food Biotechnology, Inc., at its facilities in O'Fallon, Mo.

All test animals will be hatched from carotenoid-deficient eggs. These are created by feeding a parental generation (designated as P1 birds) with only carotenoid-deficient feed after the birds reach maturity. Their eggs are broken open and analyzed for carotenoids until the eggs become carotenoid-deficient. Eggs which are subsequently laid by these carotenoid-deficient parental birds will be used to hatch all test and control birds.

The test and control birds are divided into four major groups, which receive different diets. These groups are designated as the C+ group, the C− group, the BC+ group, and the ZX+ group, depending on which carotenoids they receive in their diets.

Birds in the C+ group are fed a standard commercial diet which contains several carotenoids; this diet also contains synthetic alpha-tocopherol (Vitamin E) as an additive. Retinal tissue from birds which received this standard C+ diet has been analyzed to determine average baseline concentrations of a number of specific carotenoids and vitamins of interest, including zeaxanthin, lutein, β-carotene, vitamin A, and vitamin E. The baseline values for these birds are in Table 1.

Birds in the C− diet group are fed a diet which is essentially devoid of all carotenoids, as described above. However, this diet contains all other essential nutrients, and it contains synthetic vitamins A and E as additives.

Birds in the BC+ group receive a diet which is devoid of all other carotenoids, but which contains β-carotene as an additive. This will allow a direct comparison of β-carotene and zeaxanthin in protecting the retina.

Birds in the ZX+ group receive a diet which is devoid of all other carotenoids but which contains dried biomass containing the R-R isomer of zeaxanthin, from AFB's F. multivorum cells. There will be two different dosages of zeaxanthin fed to these birds; one ZX+ group will receive a relatively small quantity of zeaxanthin, averaging 5 mg of zeaxanthin per kilogram of feed. Since Japanese quail eat about 25 to 35 grams of food per day, this translates to about 125 to 175 micrograms of zeaxanthin per bird per day in the low dosage group. The ZX+ group will be fed a ten-fold higher quantity, averaging 1.25 to 1.75 milligrams of zeaxanthin per bird per day. These two different dosage levels

TABLE 1

| Results: | Compound Identified | Concentration (ng per mg) retina) |
|---|---|---|
| Retinal Extract of Japanese Quail (*Coturnix coturnix japonicum*) All birds were fed a standard commercial diet which contained significant quantities of β-Carotene. No β-Carotene was detected in these retinas. | Zeaxanthin | 4.7 |
| | Lutein | 4.0 |
| | alpha-Tocopherol | 15.6 |
| | gamma-Tocopherol | 5.0 |
| | Retinol (Vit. A) | 5.8 |
| | Canthaxanthin | 1.7 |
| | alpha-Cryptoxanthin | 1.4 |

will allow a quantitative dose-and-effect relationship to be evaluated, to correlate the quantity of zeaxanthin ingested to various indicators of retinal damage. All birds which receive zeaxanthin will be in the C− diet group, so they will not be receiving any other carotenoids.

All birds will be raised and kept in normal brooding cages. Except as noted below, they will be kept under normal broad-spectrum lighting of about 200 lux intensity, 14 hours on and 10 hours off each day.

Some of the test birds will be subjected to high-intensity light at 12,000 lux for a single period, which initially will range from 2 to 8 hours for several initial groups of trial birds. This high-intensity exposure is expected generate a level of retinal damage that will be severe in carotenoid-deficient birds while being less severe in carotenoid-normal birds. If initial tests indicate that the level of damage is either too low or too high to be optimal for analytical purposes, the exposure period will be lengthened or shortened accordingly. The light bulbs will be behind cooling devices, to ensure that ambient temperatures do not affect the outcome. Birds will be sacrificed at various times over a 7 day period after exposure to the high-intensity lights. In addition, in each of the diet and treatment groups, various birds will be sacrificed at stages which allow evaluation of the effects of diets and treatments as a function of aging.

All retinas from sacrificed birds will be analyzed quantitatively for lutein, zeaxanthin, and other carotenoids, for vitamins A and E, and for drusen and lipofuscin deposits as indicators of macular degeneration.

Based on numerous animal tests that have been reported in the scientific literature, and based upon what is known about how carotenoids function in the retina, there is every reason to believe and anticipate that Japanese quail which are fed C− diets (i.e., carotenoid-deficient diets) will display the following symptoms in their retinas: (1) they will develop substantially higher levels of drusen and lipofuscin than birds that receive C+ diets containing carotenoids; (2) they will be more susceptible to light-induced retinal damage than birds that receive a C+ diet; and (3) the extent of the damage caused by high-intensity light exposure will be more severe in C− birds than in C+ birds. These aspects of the bird tests, which involve other carotenoids rather than zeaxanthin, will confirm what has already been established many times before in tests involving other types of animals, and they will establish numerical values for Japanese quail, which will render the zeaxanthin data more useful and meaningful.

The results form the zeaxanthin tests on these birds are expected to show the following:

1. Zeaxanthin which has been synthesized by F. multivorum is digested in a normal manner, crosses the intestinal barrier, and enters the bloodstream after being fed to the birds.

2. Zeaxanthin which has been synthesized by F. multivorum is taken up by yellow-pigmented retinal cells in the birds' eyes, in sufficient quantities to help protect retinal tissue against phototoxic damage.

3. Zeaxanthin is substantially more potent and effective then either β-carotene or vitamin E in protecting the pigmented portion of the retina against light-induced damage, as evidenced by the higher potency of zeaxanthin in preventing or reducing the quantities of drusen and/or lipofuscin in the retinas of test animals exposed for prolonged periods to high intensity blue light.

4. Although any predictions about retinal aging processes in small animals that live for only about 1 to 4 years must be qualified, zeaxanthin is expected to be able to reduce drusen and/or lipofuscin accumulation in the retinas of test animals that have not been subjected to abnormal amounts of light, but which have aged to a one-year time frame, which in Japanese quail has been shown to be sufficient for demonstrating age-related accumulations of drusen and lipofuscin.

5. There is likely to be a direct dose-response relationship between the quantity of zeaxanthin which is fed to the birds, and the amount of protection provided to the retinal tissue.

Example 7

Effects of Zeaxanthin on Mature Birds That Were Previously Deprived of Carotenoids A group of Japanese quail which have been hatched from carotenoid-deficient eggs (as described above) will be raised to maturity on a diet devoid of carotenoids. After they reach middle age (at approximately 24 weeks), their diets will be supplemented with zeaxanthin from F. multivorum dried biomass, for periods ranging from ½ day to 7 days, to generate dose-response data. These birds will then be divided into different treatment groups. Some groups will be exposed to high-intensity light as described above, while other groups in control populations will be kept in regular low-intensity lighting. The birds will then be sacrificed and their retinal tissue will be examined for carotenoids, vitamins, and drusen and lipofuscin deposits, to evaluate the levels of protection provided by an zeaxanthin which has entered their retinas.

This series of tests will help determine two things: (1) whether zeaxanthin supplements are capable of protecting retinal tissue, even if the nutritional supplementation is not commenced until after the animals have passed through the infant and juvenile stages and have reached maturity; and (2) the effects of zeaxanthin dosage on protection levels. It is expected that zeaxanthin supplements will be capable of helping to protect retinal tissue against phototoxic damage and age-related macular degeneration, even if the nutritional supplementation is not commenced until after the animals have reached maturity.

Thus, there has been shown and described a new and useful means for creating zeaxanthin preparations for human ingestion, containing the R-R stereoisomer of zeaxanthin as a sole isomer and a sole carotenoid, to prevent, treat, or otherwise reduce the damage and loss of eyesight caused by macular degeneration. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Bauernfeind, J. C. (ed.), Carotenoids as Colorants and Vitamin A Precursors: Technological and Nutritional Applications (Academic Press, New York, 1981)

Bone, R. A., "The role of the macular pigment in the detection of polarized light," Vision Research 20:213–220 (1980)

Bone, R. A., et al, "Preliminary identification of the human macular pigment," Vision Res. 25: 1531–1535 (1985)

Bone, R. A., et al, "Analysis of the macular pigment by HPLC: retinal distribution and age study," Invest. Opthalmol. Vis. Sci. 29: 843–849 (1988)

Bone R. A., et al, "Stereochemistry of the macular carotenoids," Invest. Ophthalmol. Vis. Sci. 34: 2033–2040 (1993)

Bone, R. A., et al, "Distribution of macular pigment stereomers in individual eyes, including those with age-related macular degeneration (AMD)," ARVO Abstracts: Invest. Ophthalmol. Vis. Sci. 35: 1502 (1994)

di Mascio, P., et al, "Lycopene as the most efficient biological carotenoid singlet oxygen quencher," Archives of Biochemistry and Biophysics 274: 532–538 (1989)

Dorey, C. K., et al, "Lipofuscin in aged and AMD eyes," in Retinal Degeneration (Hollyfield et al, editors, Plenum Press, New York, 1993)

Eye disease Case Control Study Group, "Antioxidant status and neovascular age-related macular degeneration," Arch. Ophthalmol. 11: 104–109 (1993)

Eye Disease Case Control Study Group, "Risk factors for neovascular age-related macular degeneration," Arch. Ophthalmol. 10: 1701–1708 (1992)

Foote, C. S., et al, "Chemistry of singlet oxygen. XI. . Cis-Trans isomerization of carotenoids by singlet oxygen and a probable quenching mechanism," J. Amer. Chem. Soc. 92: 5218–5219 (1970)

Foote, C. S., et al, "Chemistry of singlet oxygen. X. Carotenoid quenching parallels biological protection," J. Amer. Chem. Soc. 92: 5216–5218 (1970)

Gerster, H., "Review: antioxidant protection of the ageing macula," Age and Aging 20: 60–69 (1991)

Gittinger, J. W., Manual of Clinical and Problem Ophthalmology (Little-Brown, Boston, 1988)

Haegerstrom-Portnoy, G., "Short-wavelength-sensitive-cone sensitivity loss with aging: a protective role for macular pigment?," J. Opt. Soc. Am. A5: 2140–2144 (1988)

Ham, W. T., Jr., et al, "Basic mechanisms underlying the production of photochemical lesions in the mammalian retina," Current Eye Research 3: 165–174 (1984)

Handelman, G. J. and Dratz, E. A., "The role of antioxidants in the retina and retinal pigment epithelium and the nature of prooxidant-induced damage," Adv. in Free Radical Biology & Medicine 2: 1–89 (1986)

Handelman, G. J., et al, "Carotenoids in the human macula and whole retina," Invest. Ophthalmol. Vis. Sci. 29: 850–855 (1988)

Jialal, L., et al, "β-Carotene inhibits the oxidative modification of low-density lipoprotein," Biochimica et Biophysica Acta 1086: 134–138 (1991)

Khachik, F., et al, "Separation, identification and quantification of carotenoids in fruits, vegetables and human plasma by high performance liquid chromatography," Pure and Applied Chemistry 63: 71–80 (1991)

Kirschfeld, K., "Carotenoid pigments: their possible role in protecting against photoxidation in eyes and photoreceptor cells," Proc. R. Soc. Lond. B 216: 71–85 (1982)

Malinow, M. R., et al, "Diet-related macular anomalies in monkeys," Invest. Ophthalmol. Vis. Sci. 19: 857–863 (1980)

Olson, J. A., "Absorption, transport, and metabolism of carotenoids in humans," Pure and Applied Chemistry 66:5 1011–1016 (1994)

Pease, P. L., et al, "Optical density of human macular pigment," Vision Res. 27: 705–710 (1987)

Peto, R., et al, "Can dietary beta-carotene materially reduce human cancer rates?" Nature 290: 201–208 (1981)

Schalch, W., "Carotenoids in the retina—a review of their possible role in preventing or limiting damage caused by light and oxygen," EXS 62: 280–298 (1992)

Seddon, J. M., et al, "Dietary carotenoids, vitamins A, C, and E, and advanced age-related macular degeneration," JAMA 272: 1413–1420 (1994)

Snodderly, D. M., et al, "The macular pigment. I. Absorbance spectra, localization, and discrimination from other yellow pigments in primate retinas," Invest. Ophthalmol. Vis. Sci. 25: 660–673 (1984)

Sperduto, R. D., et al, "Do we have a nutritional treatment for age-related cataract or macular degeneration→," Arch. Ophthalmol. 108: 1403–1405 (1990)

Taylor, A., et al, "Oxidation and aging: impact on vision," Journal of Toxicology and Industrial Health 9: 349–371 (1993)

Vaughn, D. and Asbury, T., General Ophthalmology, 13th ed. (Appleton and Lange, Norwalk, Conn., 1992)

Wald, G.,"The photochemistry of vision," Doc. Ophthalmol. 3: 94 (1949)

Weiter, J. J., et al, "Central sparing in annular macular degeneration," Am. J. Ophthalmol. 106: 286–292 (1988)

Werner, J. S., et al, "Aging and human macular pigment density," Vision Res. 27: 257–268 (1987)

We claim:

1. A composition of matter comprising a digestible watertight capsule and a fluid contained therein, wherein the capsule and fluid are sized and designed for oral ingestion by a human and are pharmacologically acceptable, wherein the fluid contains a 3R-3'R stereoisomer of zeaxanthin, wherein the 3R-3'R stereoisomer of zeaxanthin constitutes at least about 90 percent of all zeaxanthin in the fluid while S-S and S-R stereoisomers constitute less than about 10 percent of all zeaxanthin in the fluid, and wherein the capsule contains at least about 3 milligrams of the 3R-3'R stereoisomer of zeaxanthin.

2. The composition of claim 1 wherein the fluid contains no detectable quantity of S-S and R-S stereoisomers of zeaxanthin, and wherein the 3R-3'R stereoisomer of zeaxanthin is present as a sole detectable stereoisomer of zeaxanthin.

3. The composition of claim 1 wherein the capsule contains at least about 10 milligrams of the 3R-3'R stereoisomer of zeaxanthin.

4. The composition of claim 1 wherein the 3R-3'R stereoisomer of zeaxanthin constitutes at least about 90 percent by weight of total carotenoids in the fluid, and wherein other carotenoids which might compete against zeaxanthin for alimentary uptake or tissue deposition after ingestion constitute less than about 10 percent, by weight, of total carotenoids in the drug formulation.

5. The composition of claim 1 wherein the 3R-3'R stereoisomer of zeaxanthin is synthesized by a method which comprises the step of culturing, under conditions which promote zeaxanthin biosynthesis, bacterial cells descended from a strain of Flavobacterium multivorum which has been given ATCC accession number 55238.

6. The composition of claim 1 wherein the 3R-3'R stereoisomer of zeaxanthin is synthesized by culturing, under conditions which promote zeaxanthin biosynthesis, cells which have been genetically engineered to contain at least one zeaxanthin-synthesis gene containing a DNA sequence obtained from cells descended from a strain of Flavobacterium multivorum which has been given ATCC accession number 55238.

7. The composition of claim 1 wherein the 3R-3'R stereoisomer of zeaxanthin is enclosed within micelles that were created using a bile salt.

8. A composition of matter comprising a tablet designed for oral ingestion by a human, wherein the tablet contains:

a. a 3R-3'R stereoisomer of zeaxanthin, and b. a compressible binder material which is compatible with zeaxanthin and which causes a mixture of zeaxanthin and the binder material to retain its shape after compression under suitable pressure, and wherein the tablet is pharmacologically acceptable and sized for oral ingestion by a human, and wherein the 3R-3'R stereoisomer of zeaxanthin constitutes at least about 90 percent of all zeaxanthin in the tablet while S-S and S-R stereoisomers constitute less than about 10 percent of all zeaxanthin in the tablet, and wherein the [capsule] *tablet* contains at least about 3 milligrams of the 3R-3'R stereoisomer of zeaxanthin.

9. The composition of matter of claim 8, wherein the tablet is enclosed within a digestible coating layer that helps protect the zeaxanthin against oxidation.

10. A composition of matter comprising a formulation that is intended for oral ingestion by humans, wherein the formulation contains:

a. a nutritionally acceptable and tasteful food substance for human consumption as a carrier for zeaxanthin, and b. a 3R-3'R stereoisomer of zeaxanthin which has been added to the food substance as a nutritional additive, in a quantity sufficient to provide a concentration of at least about 1% zeaxanthin by weight, wherein the 3R-3'R stereoisomer of zeaxanthin constitutes at least about 90 percent of all zeaxanthin in the food substance while S-S and S-R stereoisomers constitute less than about 10 percent of all zeaxanthin in the food substance.

11. The composition of matter of claim 10 wherein the food substance is selected from the group consisting of margarine, dairy products, syrup, baked foodstuffs, cookie dough, brownie batter, meat preparations, and soup ingredients.

12. The composition of matter of claim 10 wherein the zeaxanthin is microencapsulated and is enclosed within a protective coating that reduces degradation of the zeaxanthin by stomach acid.

13. The composition of matter of claim 10 wherein the food substance comprises a granula formulation.

14. The composition of matter of claim 13 wherein the granular formulation is selected from the group consisting of salt-containing flavoring mixtures, spice-containing flavoring mixtures, soup additives, baking mixes, and flavored additives for milk.

15. The composition of matter of claim 13 wherein the zeaxanthin in the granular formulation is enclosed within a protective coating that reduces degradation of the zeaxanthin by stomach acid.

16. The composition of matter of claim 10 wherein the foodstuff is selected from the group consisting of cheese, yogurt, milk, and beer.

17. A composition of matter comprising a digestible watertight capsule and a fluid contained therein, wherein the capsule and fluid are sized and designed for oral ingestion by a human and are pharmacologically acceptable, wherein the fluid contains a 3R-3'R stereoisomer of zeaxanthin, wherein the 3R-3'R stereoisomer of zeaxanthin constitutes at least about 90 percent of all zeaxanthin in the fluid while S-S and S-R stereoisomers constitute less than about 10 percent of all zeaxanthin in the fluid, and wherein at least a portion of the zeaxanthin in the capsule is created by a step comprising fermentation of cells which synthesize zeaxanthin.

18. A composition of matter comprising a tablet designed for oral ingestion by a human, wherein the tablet contains:

a. a 3R-3'R stereoisomer of zeaxanthin, and b. a compressible binder material which is compatible with zeaxanthin and which causes a mixture of zeaxanthin and the binder material to retain its shape after compression under suitable pressure, and wherein the tablet is pharmacologically acceptable and sized for oral ingestion by a human, and wherein the 3R-3'R stereoisomer of zeaxanthin constitutes at least about 90 percent of all zeaxanthin in the tablet while S-S and S-R stereoisomers constitute less than about 10 percent of all zeaxanthin in the tablet, and wherein at least a portion of the zeaxanthin in the [capsule] *tablet* is created by a step comprising fermentation of cells which synthesize zeaxanthin.

*19. A composition of matter comprising a digestible watertight capsule and a fluid contained therein, wherein the capsule and fluid are sized and designed for oral ingestion by a human and are pharmacologically acceptable, wherein the fluid contains a 3R-3'R stereoisomer of zeaxanthin, wherein the 3R-3'R stereoisomer of zeaxanthin constitutes at least about 90 percent of all zeaxanthin in the fluid while S-S and S-R stereoisomers constitute less than about 10 percent of all zeaxanthin in the fluid, and wherein the capsule contains a sufficient quantity of the 3R-3'R stereoisomer of zeaxanthin to treat or retard macular degeneration when used as a drug by patients suffering from macular degeneration.*

*20. The composition of matter of claim 19, wherein the capsule contains the 3R-3'R stereoisomer of zeaxanthin at a concentration of at least about 2 percent, by weight.*

*21. The composition of matter of claim 19, wherein the capsule contains at least about 3 milligrams of the 3R-3'R stereoisomer of zeaxanthin.*

*22. A composition of matter comprising a digestible watertight capsule and a fluid contained therein, wherein the capsule and fluid are sized and designed for oral ingestion by a human and are pharmacologically acceptable, wherein the fluid contains a 3R-3'R stereoisomer of zeaxanthin, where the 3R-3'R stereoisomer of zeaxanthin constitutes at least about 90 percent of all zeaxanthin in the fluid while S-S and S-R stereoisomers constitute less than about 10 percent of all zeaxanthin in the fluid, and wherein the capsule contains a sufficient quantity of the 3R-3'R stereoisomer of zeaxanthin to reduce long-term risk of macular degeneration in humans.*

*23. The composition of matter of claim 19, wherein the capsule contains a quantity of the 3R-3'R stereoisomer of zeaxanthin in a range of about 0.5 to 25 milligrams.*

*24. A nutritional supplement, comprising a 3R-3'R stereoisomer of zeaxanthin in a digestible capsule or tablet designed and sized for human ingestion, wherein the 3R-3'R stereoisomer of zeaxanthin constitutes at least about 90 percent of all zeaxanthin while S-S and S-R stereoisomers constitute less than about 10 percent of all zeaxanthin, and wherein the 3R-3'R stereoisomer of zeaxanthin constitutes at least about 90 percent of total carotenoids in the capsule or tablet, and wherein other carotenoids which might compete against zeaxanthin for alimentary uptake or tissue deposition after ingestion constitute less than about 10 percent, by weight, of total carotenoids in the capsule or tablet, and wherein the capsule or tablet contains a sufficient quantity of the 3R-3'R stereoisomer of zeaxanthin to reduce long-term risk of macular degeneration when such capsules or tablets are taken daily by humans.*

*25. A nutritional supplement, comprising a 3R-3'R stereoisomer of zeaxanthin in a digestible capsule or tablet designed and sized for human ingestion, wherein the 3R-3'R stereoisomer of zeaxanthin constitutes at least about 90 percent of all zeaxanthin while S-S and S-R stereoisomers constitute less than about 10 percent of all zeaxanthin, and wherein the 3R-3'R stereoisomer of zeaxanthin constitutes at least about 90 percent of total carotenoids in the capsule or tablet, and wherein other carotenoids which might compete against zeaxanthin for alimentary uptake or tissue deposition after ingestion constitute less than about 10 percent, by weight, of total carotenoids in the capsule or tablet, and wherein the capsule or tablet contains at least about 0.5 milligrams of the 3R-3'R stereoisomer of zeaxanthin.*

*26. A nutritional supplement, comprising a 3R-3'R stereoisomer of zeaxanthin in a digestible capsule or tablet designed and sized for human ingestion, wherein the capsule or tablet contains a 3R-3'R stereoisomer of zeaxanthin, wherein the 3R-3'R stereoisomer of zeaxanthin constitutes at least about 90 percent of all zeaxanthin in the capsule or tablet while S-S and S-R stereoisomers constitute less than about 10 percent of all zeaxanthin, and wherein the capsule or tablet contains a sufficient quantity of the 3R-3'R stereoisomer of zeaxanthin to cause deposition of detectable quantities of additional zeaxanthin in retinal tissue if one capsule or tablet is ingested daily.*

*27. The composition of matter of claim 26, wherein the 3R-3'R stereoisomer of zeaxanthin constitutes at least about 90 percent of all carotenoids in the capsule or tablet.*

*28. A nutritional supplement, comprising a 3R-3'R stereoisomer of zeaxanthin in a digestible capsule or tablet designed and sized for human ingestion, wherein the 3R-3'R stereoisomer of zeaxanthin constitutes at least about 90 percent of all zeaxanthin while S-S and S-R stereoisomers constitute less than about 10 percent of all zeaxanthin, and wherein the 3R-3'R stereoisomer of zeaxanthin constitutes at least about 90 percent of total carotenoids in the capsule or tablet, and wherein other carotenoids constitute less than about 10 percent, by weight, of total carotenoids in the capsule or tablet.*

*29. The nutritional supplement of claim 28, wherein the capsule or tablet contains at least about 0.5 milligrams of the 3R-3'R stereoisomer of zeaxanthin.*

*30. A nutritional supplement, comprising a 3R-3'R stereoisomer of zeaxanthin in a digestible capsule or tablet designed and sized for human ingestion, wherein the 3R-3'R stereoisomer of zeaxanthin constitutes at least about 90 percent of all zeaxanthin while S-S and S-R stereoisomers constitute less than about 10 percent of all zeaxanthin, and wherein the capsule or tablet contains at least about 0.5 milligrams of the 3R-3'R stereoisomer of zeaxanthin.*

*31. A nutritional supplement, comprising a 3R-3'R stereoisomer of zeaxanthin in a digestible capsule or tablet designed and sized for human ingestion, wherein the 3R-3'R stereoisomer of zeaxanthin constitutes at least about 90 percent of all zeaxanthin while S-S and S-R stereoisomers constitute less than about 10 percent of all zeaxanthin.*

*32. The nutritional supplement of claim 31, wherein the capsule or tablet contains at least about 0.5 milligrams of the 3R-3'R stereoisomer of zeaxanthin.*

*33. A nutritional supplement, comprising a 3R-3'R stereoisomer of zeaxanthin in a digestible capsule or tablet designed and sized for human ingestion, wherein the capsule or tablet contains a 3R-3'R stereoisomer of zeaxanthin, wherein the 3R-3'R stereoisomer of zeaxanthin constitutes at least about 90 percent of all zeaxanthin in the capsule or tablet while S-S and S-R stereoisomers constitute less than about 10 percent of all zeaxanthin, and wherein the capsule or tablet contains a sufficient quantity of the 3R-3'R stereoisomer of zeaxanthin to cause a detectable increase in zeaxanthin concentration in retinal tissue if one capsule or tablet is ingested daily.*

* * * * *

UNITED STATES PATENT AND TRADEMARK OFFICE

CERTIFICATE OF CORRECTION

PATENT NO. : RE 38,009 E 
APPLICATION NO. : 09/699985
DATED : February 25, 2003
INVENTOR(S) : Kevin M. Garnett et al.

It is certified that error appears in the above-identified patent and that said Letters Patent is hereby corrected as shown below:

On the title page, column 2, delete Daniel Burnham and Ronald Compton from Item 74, "Attorney, Agent or Firm"

On pages 2 and 3 on title page item [56], in the listing of prior art references, it should be noted that there are two distinct blocks of listings, and each block has its own alphabetic order, which might lead to confusion among some readers. For example, one article by Seddon et al in 1994 (in JAMA, the *Journal of the American Medical Association*) is listed on page 2, while another article by Seddon et al in 1994 (in IOVS, *Investigative Ophthalmology and Visual Sciences*) is listed on page 3.

Col. 2, lines 2-3, "Accumulations" should be -- Accumulation --
Col. 3, line 11, "As" should be -- as --
Col. 8, line 11, "sealed" should be -- scaled --
Col. 10, line 37, "with R-R" should be -- with the R-R --
Col. 11, line 16, "coating" should be -- coated --
Col. 11, line 53, "descried" should be -- described --
Col. 12, line 48, "the macular" should be -- the macula --
Col. 12, line 51, "sunlight may" should be -- sunlight, may --
Col. 13, line 16, "safety" should be -- safely --
Col. 13, line 48, "isomer zeaxanthin" should be -- isomer of zeaxanthin --
Col. 14, line 61, "sugar of syrup" should be -- sugar or syrup --
Col. 16, line 2, the second "250 µg/L" should be -- 250 mg/L --
Col. 16, line 28, "lyophilization at 25°C" should be -- lyophilization at -25°C --
Col. 20, line 19, "results form" should be -- results from --
Col. 20, line 30, "then" should be -- than --
Col. 20, line 66, "an" should be -- any --

UNITED STATES PATENT AND TRADEMARK OFFICE

CERTIFICATE OF CORRECTION

PATENT NO. : RE 38,009 E
APPLICATION NO. : 09/699985
DATED : February 25, 2003
INVENTOR(S) : Kevin M. Garnett et al.

It is certified that error appears in the above-identified patent and that said Letters Patent is hereby corrected as shown below:

Col. 23 line 18 in claim 4, “the drug formulation” has no antecedent, and should read -- the fluid --

Col. 24 line 10 in claim 13, “granula” should read -- granular --

Signed and Sealed this

Fourth Day of March, 2008

JON W. DUDAS
*Director of the United States Patent and Trademark Office*